United States Patent
Faries, Jr. et al.

(10) Patent No.: US 6,918,395 B2
(45) Date of Patent: Jul. 19, 2005

(54) THERMAL TREATMENT SYSTEM AND METHOD FOR CONTROLLING THE SYSTEM REMOTELY TO THERMALLY TREAT STERILE SURGICAL LIQUID

(75) Inventors: Durward I. Faries, Jr., McLean, VA (US); Bruce R. Heymann, Vienna, VA (US)

(73) Assignee: O.R. Solutions, Inc., Chantilly, VA (US)

( * ) Notice: Subject to any disclaimer, the term of this patent is extended or adjusted under 35 U.S.C. 154(b) by 476 days.

(21) Appl. No.: 10/122,414

(22) Filed: Apr. 16, 2002

(65) Prior Publication Data

US 2002/0185136 A1 Dec. 12, 2002

Related U.S. Application Data

(63) Continuation of application No. 09/572,903, filed on May 17, 2000, now Pat. No. 6,371,121.

(51) Int. Cl.$^7$ ................................................ A61F 19/00
(52) U.S. Cl. .......................................... 128/849; 62/66
(58) Field of Search ........................ 128/849, 850–856; 62/66, 68, 340, 342

(56) References Cited

U.S. PATENT DOCUMENTS

| | | |
|---|---|---|
| 2,613,511 A | 10/1952 | Walsh |
| 3,869,596 A | 3/1975 | Howie |
| 3,902,484 A | 9/1975 | Winters |
| 4,270,067 A | 5/1981 | Thomas et al. |
| 4,284,880 A | 8/1981 | Keiser |
| 4,393,659 A | 7/1983 | Keyes et al. |
| 4,458,139 A | 7/1984 | McClean |
| 4,474,016 A | 10/1984 | Winchell |
| 4,522,041 A | 6/1985 | Menzel |
| 4,625,098 A | 11/1986 | Joe |
| 4,782,835 A | 11/1988 | Bernardini |
| 4,828,876 A | 5/1989 | Ohhara et al. |
| 4,869,271 A | 9/1989 | Idris |

(Continued)

FOREIGN PATENT DOCUMENTS

| | | |
|---|---|---|
| JP | 61-185967 | 8/1986 |
| JP | 06-123532 | 5/1994 |

*Primary Examiner*—Michael A. Brown
(74) *Attorney, Agent, or Firm*—Edell, Shapiro & Finnan

(57) ABSTRACT

A thermal treatment system for thermally treating a sterile medium is controlled via a foot actuated switch to thermally treat the sterile medium to a desired temperature and/or form (e.g., slush). The thermal treatment system includes a basin recessed in a system top surface, while a surgical sterile drape is placed over the system and within the basin to form a drape container for containing the sterile medium. The basin may be configured to cool the sterile medium and form sterile surgical slush, or heat the sterile medium to provide warm sterile liquid. A dislodgment mechanism may be employed within a cooling basin to manipulate the drape and dislodge frozen pieces of sterile medium adhered to the drape. Information pertaining to the sterile medium and system operation may be displayed on a system display that has dimensions sufficient to provide visibility of the information to users located within extended ranges from the system. Alternatively, the thermal treatment system may be responsive to a remote control unit to enable users to control operation of the system remotely. The remote control unit may control various operating parameters and features of the system, and preferably emits system commands in the form of code signals. A receiver is employed by the thermal treatment system to receive the transmitted signals and facilitate system operation in response to those signals. In addition, the foot actuated switch and remote control unit may be utilized with thermal treatment systems having a plurality of heating and/or cooling basins.

20 Claims, 10 Drawing Sheets

U.S. PATENT DOCUMENTS

| | | |
|---|---|---|
| 4,903,710 A | 2/1990 | Jessamine et al. |
| 4,934,152 A | 6/1990 | Templeton |
| 4,967,061 A | 10/1990 | Weber, Jr. et al. |
| 5,040,699 A | 8/1991 | Gangemi |
| 5,042,455 A | 8/1991 | Yue et al. |
| 5,129,033 A | 7/1992 | Ferrara et al. |
| 5,163,299 A | 11/1992 | Faries, Jr. et al. |
| 5,174,306 A | 12/1992 | Marshall |
| 5,310,524 A | 5/1994 | Campbell et al. |
| 5,331,820 A | 7/1994 | Faries, Jr. et al. |
| 5,333,326 A | 8/1994 | Faries, Jr. et al. |
| 5,345,063 A | 9/1994 | Reusche et al. |
| 5,363,746 A | 11/1994 | Gordon |
| 5,374,813 A | 12/1994 | Shipp |
| 5,383,476 A | 1/1995 | Peimer et al. |
| 5,386,835 A | 2/1995 | Elphick et al. |
| 5,400,267 A | 3/1995 | Denen et al. |
| 5,400,616 A | 3/1995 | Faries, Jr. et al. |
| 5,402,644 A | 4/1995 | Faries, Jr. et al. |
| 5,429,801 A | 7/1995 | Faries, Jr. et al. |
| 5,435,322 A | 7/1995 | Marshall |
| 5,443,082 A | 8/1995 | Mewburn |
| 5,449,892 A | 9/1995 | Yamada |
| 5,457,962 A | 10/1995 | Faries, Jr. et al. |
| 5,463,213 A | 10/1995 | Honda |
| 5,502,980 A | 4/1996 | Faries, Jr. et al. |
| 5,522,095 A | 6/1996 | Faries, Jr. et al. |
| 5,524,478 A | 6/1996 | Joy et al. |
| 5,524,643 A | 6/1996 | Faries, Jr. et al. |
| 5,531,697 A | 7/1996 | Olsen |
| 5,539,185 A | 7/1996 | Polster |
| 5,551,240 A | 9/1996 | Faries, Jr. et al. |
| 5,615,423 A | 4/1997 | Faries, Jr. et al. |
| 5,653,938 A | 8/1997 | Faries, Jr. et al. |
| 5,658,478 A | 8/1997 | Roeschel et al. |
| 5,664,582 A | 9/1997 | Szymaitiz |
| 5,712,460 A | 1/1998 | Carr et al. |
| 5,717,188 A | 2/1998 | Vaillancourt |
| 5,800,352 A | 9/1998 | Ferre et al. |
| 5,809,788 A | 9/1998 | Faries, Jr. et al. |
| 5,816,252 A | 10/1998 | Faries, Jr. et al. |
| 5,857,467 A | 1/1999 | Faries, Jr. et al. |
| 5,862,672 A | 1/1999 | Faries, Jr. et al. |
| 5,879,621 A | 3/1999 | Faries, Jr. et al. |
| 5,950,438 A | 9/1999 | Faries, Jr. et al. |
| 6,003,328 A | 12/1999 | Faries, Jr. et al. |
| 6,035,855 A | 3/2000 | Faries, Jr. et al. |
| 6,087,636 A | 7/2000 | Faries, Jr. et al. |
| 6,091,058 A | 7/2000 | Faries, Jr. et al. |
| 6,255,627 B1 | 7/2001 | Faries, Jr. et al. |
| 6,371,121 B1 * | 4/2002 | Faries ........................ 128/849 |
| 6,810,881 B2 | 11/2004 | Faries, Jr. et al. |
| 2003/0231990 A1 | 12/2003 | Faries, Jr. et al. |
| 2004/0200480 A1 | 10/2004 | Faries, Jr. et al. |
| 2004/0200483 A1 | 10/2004 | Faries, Jr. et al. |
| 2004/0208780 A1 | 10/2004 | Faries, Jr. et al. |

* cited by examiner

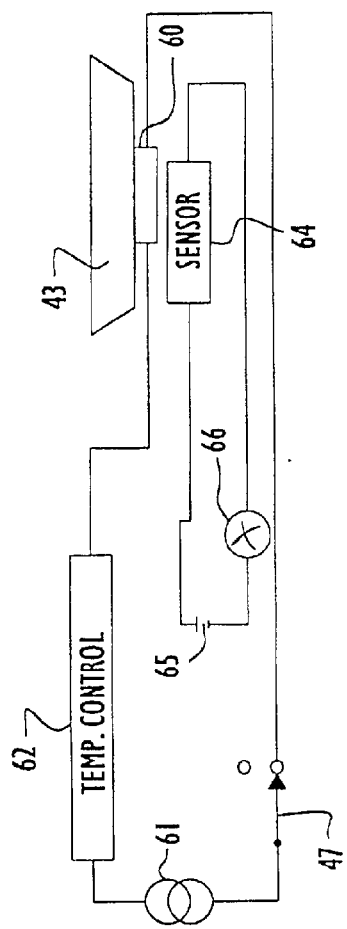
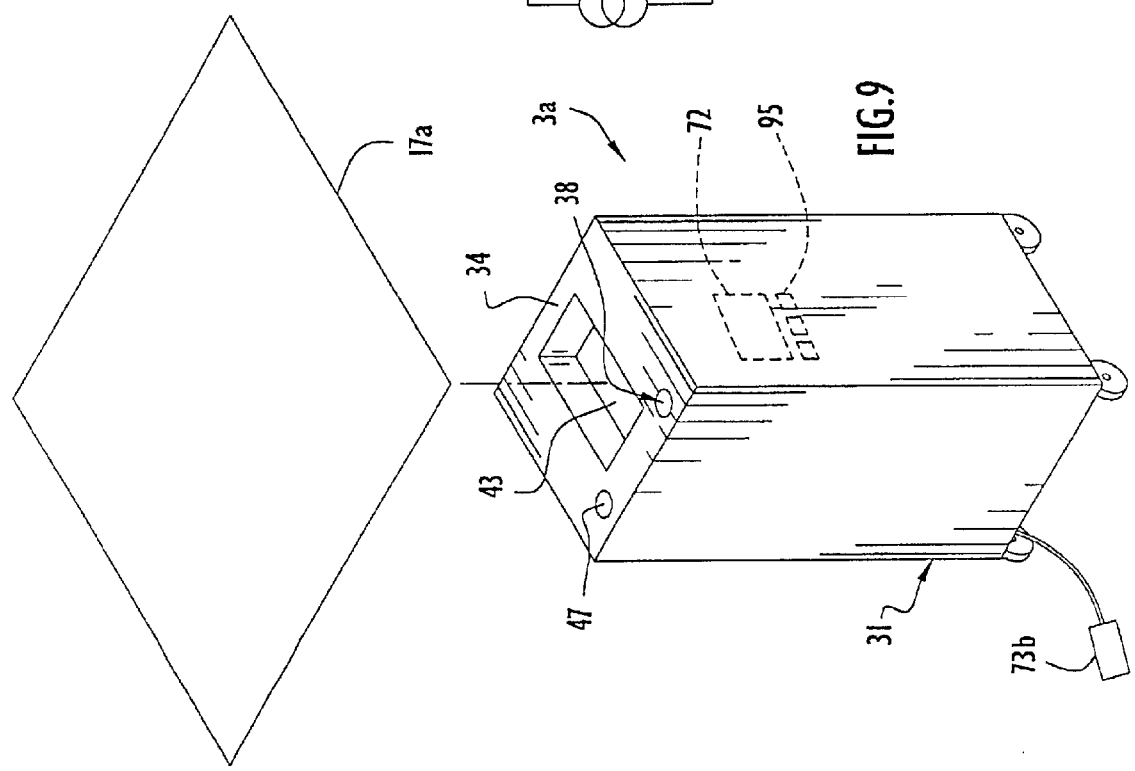

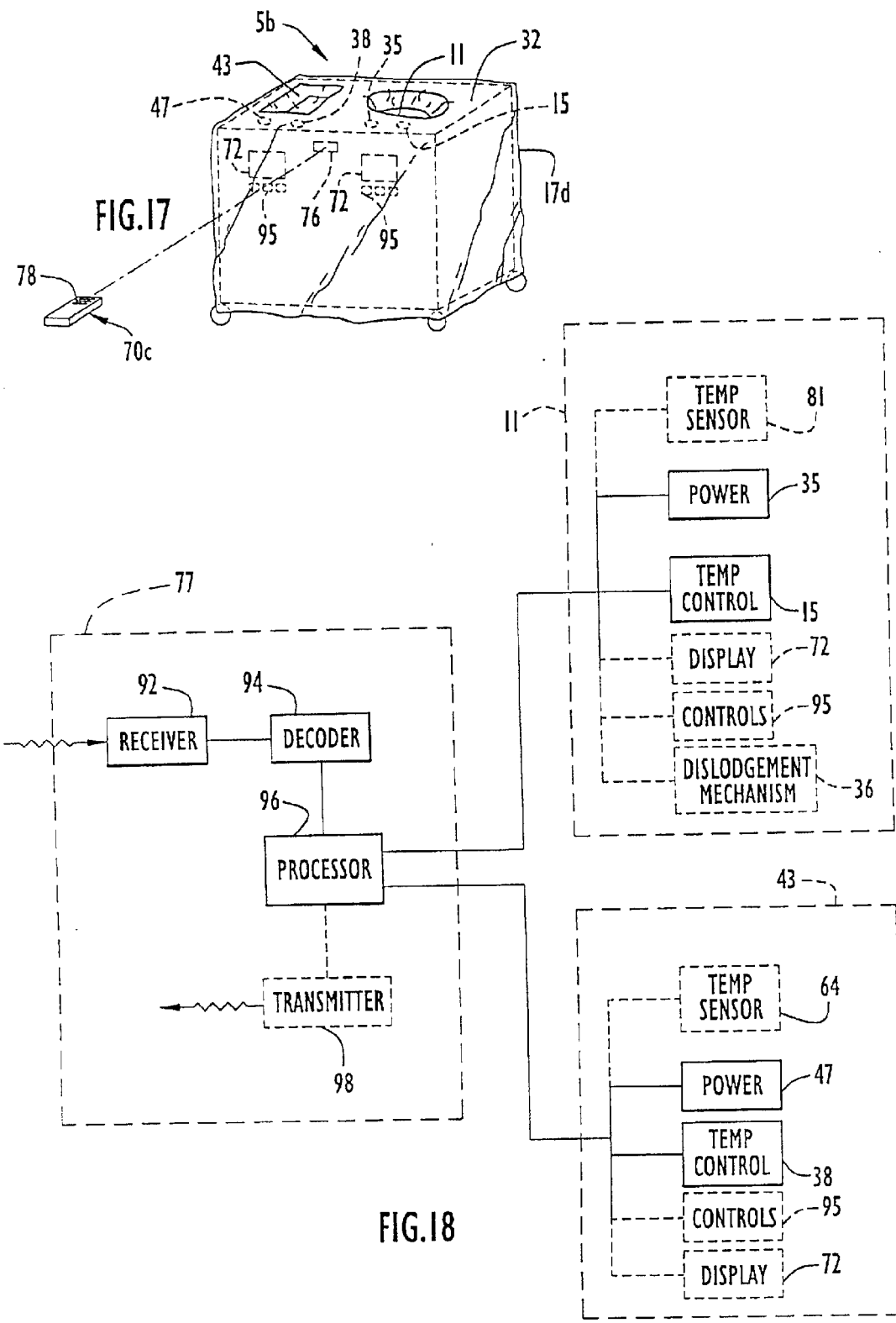

THERMAL TREATMENT SYSTEM AND METHOD FOR CONTROLLING THE SYSTEM REMOTELY TO THERMALLY TREAT STERILE SURGICAL LIQUID

CROSS REFERENCE TO RELATED APPLICATIONS

This application is a continuation of U.S. patent application Ser. No. 09/572,903, entitled "Remote Controlled Thermal Treatment System and Method for Controlling the System Remotely to Thermally Treat Sterile Surgical Liquid", and filed May 17, 2000 now U.S. Pat. No. 6,371,121. The disclosure in the above-referenced patent application is incorporated herein by reference in its entirety.

BACKGROUND OF THE INVENTION

1. Technical Field

The present invention pertains to improvements in methods and apparatus for heating and/or cooling sterile surgical media or liquids and collecting surgical sterile slush. In particular, the present invention pertains to remote control of thermal treatment systems to heat and/or cool sterile surgical media or liquids, and is an improvement of the methods and apparatus disclosed in U.S. Pat. No. 4,393,659 (Keyes et al), U.S. Pat. No. 4,934,152 (Templeton), U.S. Pat. No. 5,163,299 (Faries, Jr. et al), U.S. Pat. No. 5,331,820 (Faries, Jr. et al), U.S. Pat. No. 5,333,326 (Faries, Jr. et al), U.S. Pat. No. 5,400,616 (Faries, Jr. et al), U.S. Pat. No. 5,402,644 (Faries, Jr. et al), U.S. Pat. No. 5,429,801 (Faries, Jr. et al), U.S. Pat. No. 5,457,962 (Faries, Jr. et al), U.S. Pat. No. 5,502,980 (Faries, Jr. et al), U.S. Pat. No. 5,522,095 (Faries, Jr. et al), U.S. Pat. No. 5,524,643 (Faries, Jr. et al), U.S. Pat. No. 5,551,240 (Faries, Jr. et al), U.S. Pat. No. 5,615,423 (Faries, Jr. et al), U.S. Pat. No. 5,653,938 (Faries, Jr. et al), U.S. Pat. No. 5,809,788 (Faries, Jr. et al), U.S. Pat. No. 5,816,252 (Faries, Jr. et al), U.S. Pat. No. 5,857,467 (Faries, Jr. et al), U.S. Pat. No. 5,862,672 (Faries, Jr. et al), U.S. Pat. No. 5,879,621 (Faries, Jr. et al), U.S. Pat. No. 5,950,438 (Faries, Jr. et al), U.S. Pat. No. 6,003,328 (Faries, Jr. et al), U.S. Pat. No. 6,035,855 (Faries, Jr. et al) and copending U.S. patent application Ser. No. 08/807,095, filed Feb. 27, 1997 and entitled "Surgical Drape and Stand for Use in Heated Thermal Treatment Basins", and Ser. No. 09/046,090, filed Mar. 23, 1998 and entitled "Thermal Treatment System and Method for Maintaining Integrity and Ensuring Sterility of Surgical Drapes Used with Surgical Equipment". The disclosures in the above-mentioned patents and copending applications are incorporated herein by reference in their entireties.

2. Discussion of the Related Art

The above-referenced Keyes et al U.S. Pat. No. 4,393,659 discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton U.S. Pat. No. 4,934,152, the Keyes et al system has a number of disadvantages. In particular, the separate product basin must be removed and re-sterilized after each use. Additionally, the glycol or other thermal transfer medium is highly flammable or toxic and, in any event, complicates the procedure. The Templeton U.S. Pat. No. 4,934,152 discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al U.S. Pat. No. 5,163,299 notes that scraping congealed liquid from the drape is undesirable in view of the potential for damage to the drape, resulting in a compromise of sterile conditions. As a solution to the problem, the Faries, Jr. et al U.S. Pat. No. 5,163,299 proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel. Accordingly, several of the Faries, Jr. et al patents (e.g., U.S. Pat. Nos. 5,331,820; 5,400,616; 5,457,962; 5,502,980; 5,653,938; 5,809,788; 5,857,467; 5,950,438; 6,003,328; and 6,035,855) resolve the problem of manual drape manipulation by disclosing various techniques and/or dislodgment mechanisms to automatically remove the congealed liquid adhering to the drape without endangering the integrity of the drape.

The Templeton U.S. Pat. No. 4,934,152 further discloses an electrical heater disposed at the bottom of the basin to convert the sterile slush to warmed liquid, or to heat additional sterile liquid added to the basin. Templeton describes the need for such warm sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both warmed sterile liquid and sterile surgical slush. Accordingly, several of the Faries, Jr. et al patents (e.g., U.S. Pat. Nos. 5,333,326; 5,429,801; 5,522,095; 5,524,643; 5,615,423; 5,653,938; 5,816,252; 5,862,672; 5,857,467; and 5,879,621) disclose a manner in which to simultaneously provide both surgical slush and warmed surgical liquid during a surgical procedure by utilizing a machine having plural basins with each basin either producing surgical slush or heating a sterile liquid. This machine typically utilizes a single surgical drape that forms a drape receptacle within each basin to collect sterile slush and heated sterile liquid produced by the machine in the respective basins.

In addition, several of the drapes and thermal treatment systems disclosed in the above-mentioned patents and copending applications include specialized features to enhance various aspects of thermal treatment system operation. For example, some of the specialized features may include: bladder drapes (e.g., as disclosed in U.S. Pat. Nos. 5,809,788; 5,950,438; and 6,003,328); drapes having plates or disks (e.g., as disclosed in U.S. Pat. Nos. 5,457,962 and 5,502,980); leak detection drapes (e.g., as disclosed in U.S. Pat. Nos. 5,524,643 and 5,816,252); reinforced drapes (e.g., as disclosed in U.S. Pat. No. 5,857,467); drape indicators and corresponding thermal treatment system detection devices to ensure sterility by enabling system operation in response to detecting a sterile drape placed on the system (e.g., as disclosed in U.S. Pat. Nos. 5,653,938 and 5,879,621); drapes having indicia to direct placement of the drapes on thermal treatment systems (e.g., as disclosed in U.S. Pat. No. 5,615,423); surgical drapes constructed of materials having a coefficient of friction in a particular range and/or drapes including attachment mechanisms such that a drape may withstand being drawn under a dislodgment mechanism (e.g., as disclosed in U.S. Pat. No. 6,035,855) ; and a stand to elevate objects within a heated basin above the basin floor (e.g., as disclosed in U.S. patent application Ser. No. 08/807,095) and/or a heater configured to cover a portion of the basin (e.g., as disclosed in U.S. patent application Ser. No. 09/046,090) to prevent the drape from overheating and puncturing when objects are placed within the basin.

The above-described apparatus may stand some improvement. In particular, thermal treatment systems or machines are generally utilized for certain aspects of a medical procedure. These machines are typically operated prior to or during the medical procedure to enable a sterile medium to attain a desired temperature and/or form suitable for that procedure. The machines are positioned within an operating room or other facility proximate the medical procedure site and patient. Since the machine treats sterile media in a sterile field, sterile personnel (e.g., personnel that have taken the necessary precautions enabling them to interact with objects in the sterile field without contaminating that field) are required to operate the machine to prevent contamination of the sterile field and injury to the patient. Thus, the machine either provides sterile personnel with an additional task of controlling and monitoring the machine, or requires additional sterile personnel to perform the task, thereby increasing procedure costs and crowding the procedure site.

When the thermal treatment system is positioned within the facility beyond the proximity of the operator, personnel must physically attend to the machine to manually operate the controls. With respect to slush machines having dislodgement mechanisms, personnel may be required to repeatedly attend to the machine to operate the machine and monitor collected slush during the procedure. Further, the machine temperature indicator is generally poorly visible, and may similarly require personnel to be in close proximity to the machine to ascertain settings and liquid temperature. The process of personnel frequently attending to the thermal treatment machine may become distracting to the procedure, especially when numerous machine inspections and/or control adjustments may be required. Moreover, frequent inspections and/or adjustments may divert personnel from their medical procedure tasks at inopportune times, such as when complications arise, thereby increasing risk of injury to the patient.

In addition, operating room personnel are generally engaged in various activities during medical procedures. These activities typically include tasks ranging from monitoring and operating medical equipment to handling medical instruments. Since the personnel frequently employ their hands to perform the tasks, operation of the thermal treatment machine typically requires a current task to be completed or interrupted in order to enable personnel to utilize their hands to operate the machine controls. As a consequence, interrupted tasks may be omitted due to personnel oversight, or repeated entirely since the precise interruption point may not be recalled. This generally tends to decrease efficiency and may prevent crucial tasks from being completed at the proper time during the medical procedure, thereby risking injury to a patient.

OBJECTS AND SUMMARY OF THE INVENTION

Accordingly, it is an object of the present invention to remotely control operation of a thermal treatment system to thermally treat a sterile medium.

It is another object of the present invention to enable non-sterile personnel to remotely control operation of a thermal treatment system to thermally treat a sterile medium during a medical procedure.

Yet another object of the present invention is to display information pertaining to treatment of a sterile medium by a thermal treatment system in a manner visible to users located at extended ranges (e.g., distances extending to ten or more feet) from the system.

Still another object of the present invention is to remotely adjust various operating parameter settings of a thermal treatment system to control thermal treatment of a sterile, medium to a desired temperature and/or form (e.g., slush).

A further object of the present invention is to remotely control a thermal treatment system dislodgment mechanism to collect a desired quantity of surgical slush.

Yet another object of the present invention is to control operation of a thermal treatment system to thermally treat a sterile medium via a foot actuated switch or control unit.

The aforesaid objects are achieved individually and/or in combination, and it is not intended that the present invention be construed as requiring two or more of the objects to be combined unless expressly required by the claims attached hereto.

According to the present invention, a thermal treatment system for thermally treating a sterile medium or liquid is controlled via a foot actuated switch or control unit to thermally treat the sterile medium to a desired temperature and/or form (e.g., slush). The thermal treatment system includes a basin recessed in a system top surface, while a surgical sterile drape is placed over the system and within the basin to form a drape container for containing the sterile medium. The basin may be configured to cool the sterile medium and form sterile surgical slush, or heat the sterile medium to provide warm sterile liquid. A dislodgment mechanism may be employed within a cooling basin to manipulate the drape and dislodge frozen pieces of sterile medium adhered to the drape. Information pertaining to the sterile medium and system operation may be displayed on a system display that has dimensions sufficient to provide visibility of the information to users located within extended ranges (e.g., distances extending to ten or more feet) from the system. The foot actuated switch or control unit is in communication with the system to control system operation. The foot switch typically includes pressure sensitive transducers to facilitate entry of commands and operational parameters for transmission to the system in response to actuation of those transducers by a user.

Alternatively, the thermal treatment system may be responsive to a remote control unit to enable users to control operation of the system remotely. The remote control unit may control various operating parameters and features of the system (e.g., desired temperatures, power, display, dislodgment mechanism, etc.), and preferably emits system commands in the form of code signals. A receiver is employed by the thermal treatment system to receive the transmitted signals and facilitate system operation in response to those signals.

In addition, the foot actuated switch and remote control unit may be utilized with thermal treatment systems having a plurality of heating and/or cooling basins with each basin being individually controlled. Moreover, the systems disclosed within the above-mentioned patents and copending applications may similarly be configured to be responsive to the foot actuated switch and/or remote control unit in substantially the same manner described above.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

FIG. 9 is an exploded view in perspective of a thermal treatment system for warming a sterile medium having a surgical drape for placement thereon and a foot actuated switch to control system operation according to the present invention.

FIG. 10 is an electrical schematic diagram of a heating unit employed in the thermal treatment system of FIG. 9.

FIG. 17 is a view in perspective of a plural basin thermal treatment system having a surgical drape placed thereon and a remote control unit for controlling system operation remotely according to the present invention.

FIG. 18 is a schematic block diagram of an exemplary control circuit for the system of FIG. 17 to control system operation in response to transmitted controls from the remote control unit.

DETAILED DESCRIPTION OF THE PREFERRED EMBODIMENTS

Figure 1:
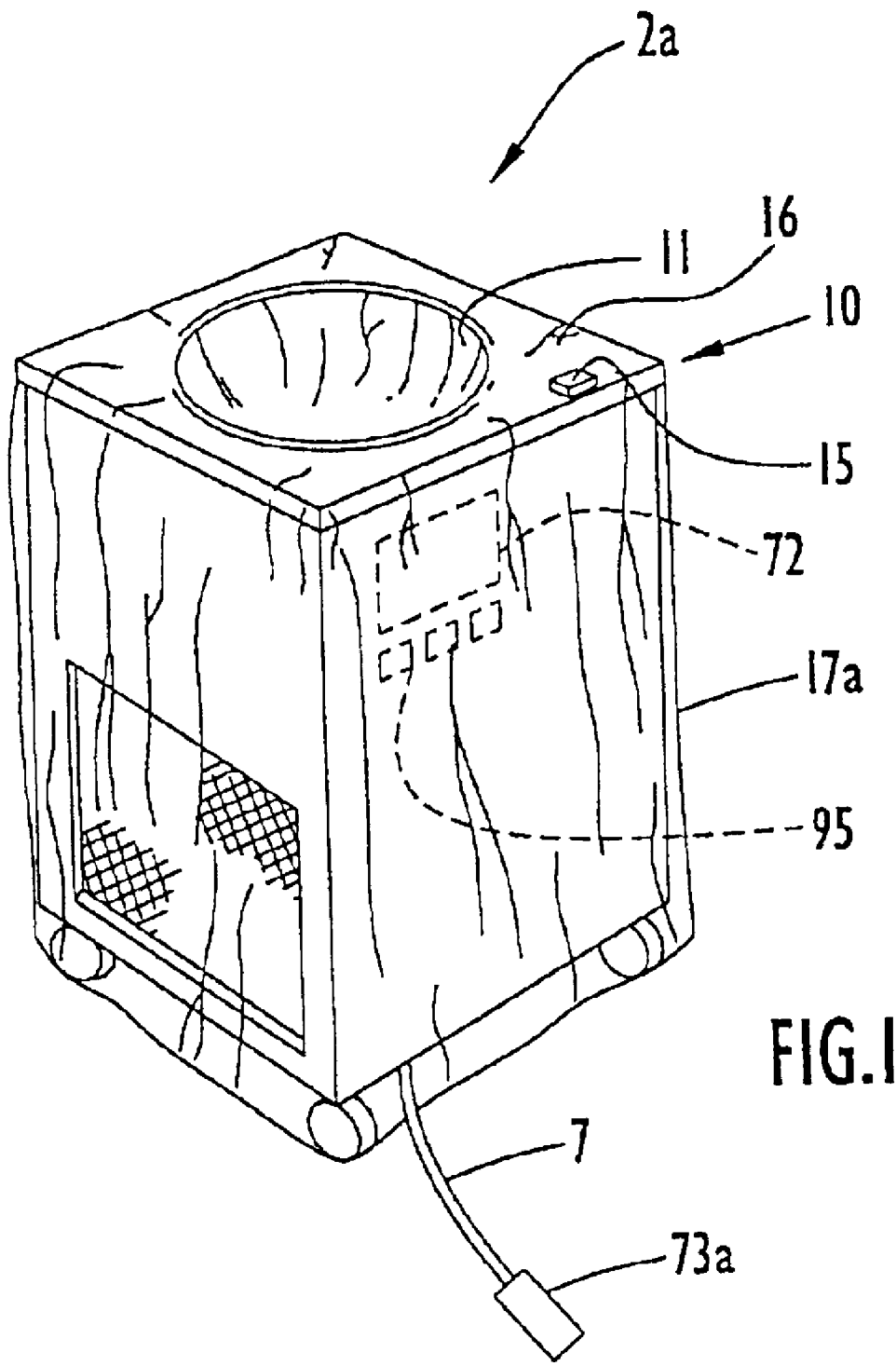
FIG. 1 is a view in perspective of a thermal treatment system for generating and collecting surgical slush having a surgical drape placed thereon and a foot actuated switch to control system operation according to the present invention.
Figure 2:
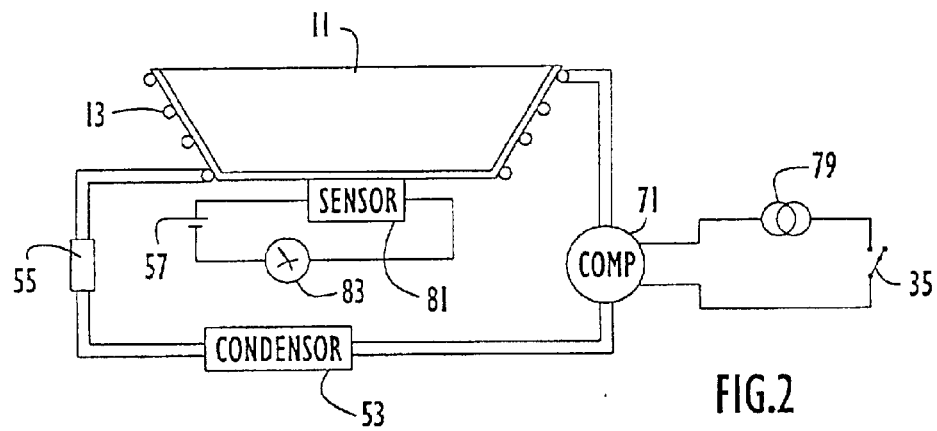
FIG. 2 is an electrical schematic diagram of the cooling system employed in the thermal treatment system of FIG. 1.

Referring to FIGS. 1–2 of the accompanying drawings, a thermal treatment system or machine 2a for cooling a sterile medium and generating surgical slush according to the present invention includes a cabinet or housing 10 with a top surface 16 having a basin 11 mounted thereon in an appropriately sized recess. Basin 11 may be of any shape, however, by way of example only, the basin is substantially circular. Basin 11 is made of thermally conductive material, typically stainless steel, and includes a generally flat bottom wall and frusto-conical side wall. A conventional refrigeration unit is disposed within cabinet 10 and typically includes a compressor 71, a condenser 53, a suitable thermal expansion valve 55 and an evaporator 13. The compressor is selectively actuable via an electrical power source 79 and an on/off power switch 35, and causes a suitable refrigerant fluid to flow through a series circuit including condenser 53, evaporator 13 and thermal expansion valve 55. The evaporator is in the form of a coil wound about the exterior surface of basin 11 in thermal transfer relation therewith to permit cooling of the basin to a desired temperature. A temperature sensor 81 is disposed along the outside surface of the basin bottom to monitor the temperature of the sterile medium and/or slush formed therein. Sensor 81 may be implemented by any conventional temperature sensor (e.g., a resistive temperature device (RTD)) and is connected in series with a voltage source 57, preferably derived from power source 79, and an indicator 83. Indicator 83 measures the current passing through sensor 81 which, in turn, is proportional to the temperature sensed in basin 11. A temperature control 15 controls the cooling of basin 11 to a desired temperature in response to the temperature measured by sensor 81. The temperature control may further include indicator 83 to provide a temperature indication. The refrigeration unit is activated via power switch 35 and temperature control 15, or via a foot actuated switch 73a, while evaporator 13 typically cools the side wall of basin 11 to a temperature substantially below the freezing temperature of the sterile liquid or medium used in forming the sterile slush. This temperature is preferably on the order of −32° F. to 10° F. For examples of the structure and operation of the refrigeration unit, reference is made to the aforementioned Keyes et al, Templeton et al and Faries, Jr. et al patents.

A sterile drape 17a, preferably transparent, is typically disposed over the top and sides of cabinet 10 and made to conform to the side wall and bottom of basin 11. Power switch 35 and temperature control 15 are disposed on top surface 16 of system cabinet 10 and are adjustable manually through drape 17a. Foot switch 73a is attached to cabinet 10 and may similarly control system operation as described below. A display 72 may be disposed on a cabinet side wall preferably toward top surface 16, while controls 95 may be disposed below the display to facilitate selective display of and/or enter desired information. The display has dimensions sufficient to enable displayed information to be perceived through the drape by users located within extended ranges (e.g., distances extending to ten or more feet) from the system, and may display any type of information pertaining to system operation (e.g., liquid or slush temperature, time, date, etc.).

The portion of drape 17a disposed in basin 11 serves as a sterile drape receptacle or container for sterile medium or liquid placed therein to be cooled and/or frozen into the desired sterile slush. Typical sterile liquid used to produce a surgical sterile slush is a 0.80% to 0.95% sodium chloride solution (e.g., saline). Drape 17a is made from a material that is impervious to the sterile liquid and sufficiently soft and flexible to conform to the basin walls. The drape may be non-fitted or flat (e.g., a plain or basic drape of sufficient length that is placed over the thermal treatment system), or may be constructed such that the drape is formed to the contour of the cabinet housing for a more precise fit (e.g., a fitted drape). The thickness of the drape is preferably minimized to render thermal transfer therethrough most efficient, yet the thickness is sufficient to resist tearing and puncturing during normal use. Typically, drape 17a is made of materials commonly used in hospitals for surgical drapes and generally has a thickness in the approximate range of three through ten mils. Drape 17a may also be made of polyurethane film as disclosed for the drape in the aforementioned Templeton patent, and may further include a preformed container portion (not shown) contoured to match the contour of a basin. The drape is designed to be disposable after a single use (e.g., a surgical procedure) and is provided presterilized and prepackaged in a manner to preserve its sterile state during storage.

Figure 3:
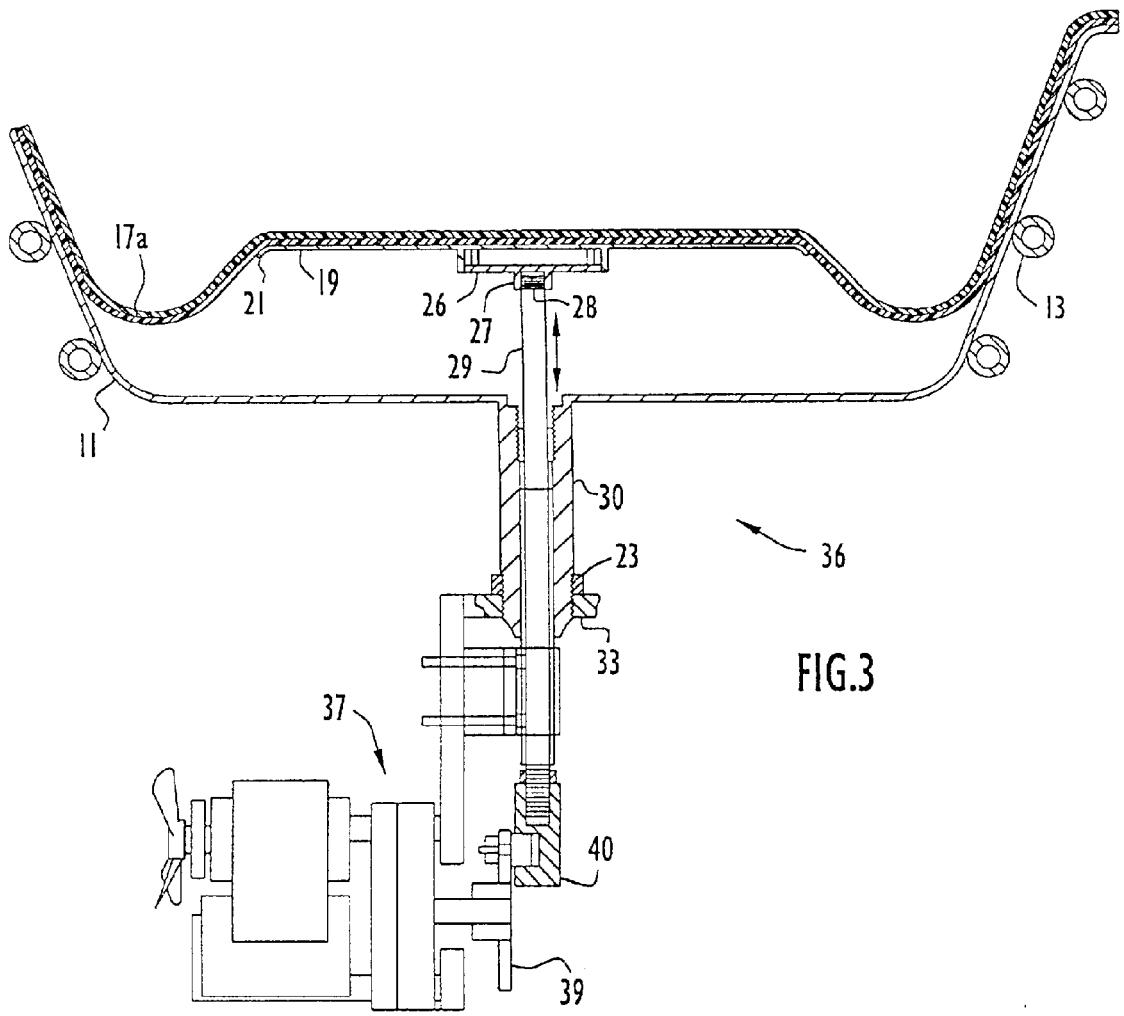
FIG. 3 is a view in elevation and partial section of a surgical drape disposed within a thermal treatment system basin having an exemplary dislodgment mechanism for manipulating the drape to dislodge congealed sterile medium adhered to the drape.

An exemplary dislodgment mechanism 36 of the. type described in the above-mentioned Faries, Jr. et al patents (e.g., U.S. Pat. Nos. 5,457,962 and 5,857,467) may be used with the system of FIG. 1 to automatically manipulate drape 17a and dislodge congealed sterile medium as illustrated in FIG. 3. Specifically, a disk or plate 19 may be bonded or attached to the drape at the underside of the drape receptacle portion and is configured to generally match the basin bottom while being supported, in a manner described below, slightly above the basin bottom between the drape and the basin. Plate 19 is generally circular with a short downturned annular lip 21 disposed at its circumference, and is configured for a snap-fit engagement with a connector plate 26. Alternatively, plate 19 may be bonded directly to the connector plate or to a shaft 29 described below with the drape receptacle bottom resting on plate 19 within the basin.

The bottom of the connector plate is provided with a centrally located downwardly depending hollow cylindrical stem 27. Stem 27 is interiorly threaded to receive a threaded tip 28 of shaft 29 extending upwardly through the bottom of basin 11. In particular, the bottom of basin 11 is provided with a central hole communicating with a bore in an adapter tube 30 secured at its upper end to the bottom of basin 11 by any convenient mechanism. The bottom end of adapter tube 30 is externally threaded and is engaged by a support bracket 33 and lock washer 23 such that bracket 33 is suspended interiorly of the machine cabinet (not shown in FIG. 3). A gear motor assembly 37 is supported by bracket 33 and includes a rotor 39 operatively engaged with a bearing track 40. Drive shaft 29 has its bottom end operatively engaged to bearing track 40 to cause the shaft to reciprocate longitudinally as rotor 39 rotates. Shaft 29 extends upwardly through adapter tube 30 and has its upper end secured to the center of the underside of connector plate 26 in the manner described above. Accordingly, as motor 37 reciprocates shaft 29 up and down, the shaft moves plate 19 up and down. Plate 19, in turn, moves the bottom of the drape container up and down to loosen pieces of frozen saline that form on the drape. The loosened pieces fall and collect in the center of the drape container as surgical slush. It is to be understood that the system of FIG. 1 may include various types of dislodgment mechanisms, such as any of those disclosed in the aforementioned Faries, Jr. et al patents.

Figure 4:
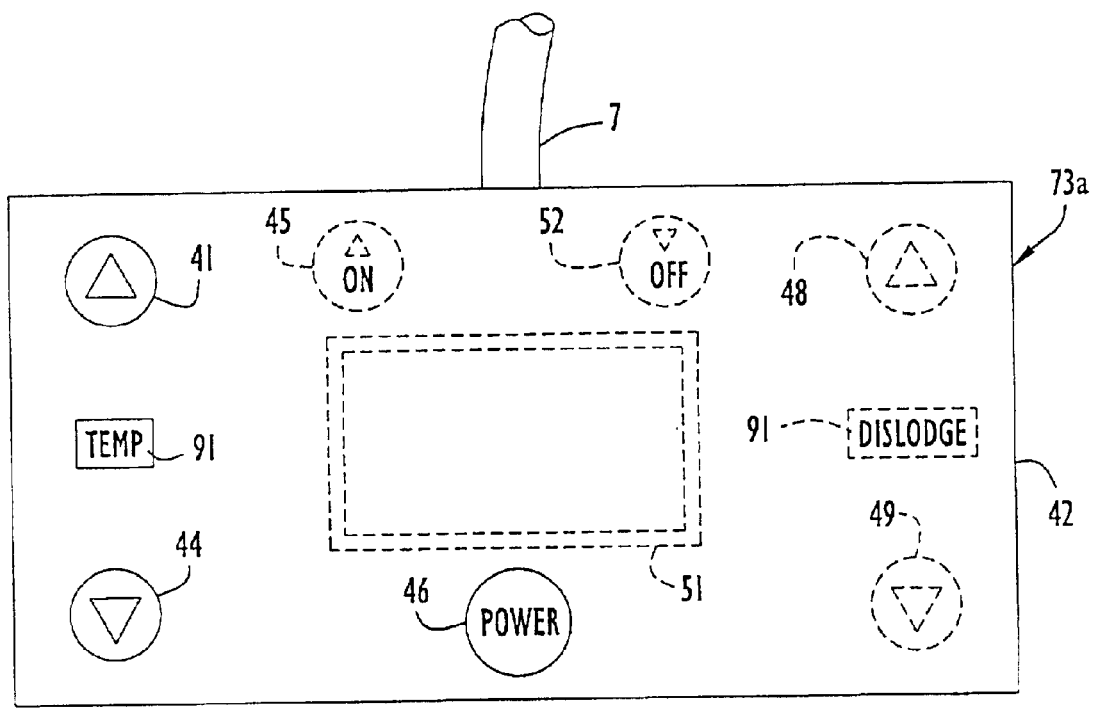
FIG. 4 is top view in plan of an exemplary foot actuated switch for the system of FIG. 1.

Generally, medical procedures are performed in an operating room or other medical facility with the assistance of various sterile and non-sterile medical personnel. The sterile personnel refer to personnel that have taken the necessary precautions enabling them to interact with objects in a sterile field without contaminating that field, while non-sterile personnel refer to personnel that have not taken those precautions and are capable of contaminating the sterile field. Since the thermal treatment system treats a sterile medium in the sterile field, sterile personnel are required to operate the system. This is due to the fact that control 15 and/or controls 95 need to be manipulated through the sterile drape during the procedure without contaminating the drape or sterile field. Further, the thermal treatments system may be positioned beyond the immediate reach of sterile personnel, or the sterile personnel may not be able to immediately control the system due to their hands being occupied by another task. Accordingly, thermal treatment system 2a may alternatively be controlled remotely via foot actuated switch 73a as illustrated, by way of example only, in FIG. 4. Specifically, foot switch 73a is coupled to thermal treatment system 2a (FIG. 1) via a cable 7 that transfers information between the foot switch and system. The foot switch includes a substantially rectangular housing 42 and several pressure sensitive transducers 41, 44 and 46 that detect switch actuation by a user as described below. The housing is constructed of suitably rigid materials to withstand pressure applied by the user during actuation and may include various indicia 91 to identify functions associated with the transducers. The non-sterile foot switch typically resides below and outside the confines of the sterile field established to prevent contamination of the medical procedure. As such, the foot switch may be disposed at various distances from the system, and may be operated by sterile or non-sterile personnel.

Transducers 41, 44 and 46 typically include substantially circular coverings having indicia to identify the particular function associated with that transducer. By way of example only, transducer 41 is disposed toward an upper left corner (e.g., as viewed in FIG. 4) of the foot switch and is actuated to increase the temperature setting for the system. Transducer 41 includes a covering having indicia in the form of an upward pointing arrow to identify the associated function. Conversely, transducer 44 is disposed below transducer 41 and is actuated to decrease the temperature setting for the system. This transducer includes a covering having indicia in the form of a downward pointing arrow to identify that function. System power may be controlled by transducer 46 disposed toward the center of the foot switch lower edge. This transducer typically includes a covering having indicia in the form of 'POWER' to indicate the associated function.

The foot switch may include additional transducers to control various other parameters of system operation. For example, transducers 45, 48, 49 and 52 maybe disposed on the foot switch to control operation of a dislodgment mechanism, such as mechanism 36 (FIG. 3). Specifically, transducers 45 and 52 are disposed above transducer 46 toward the foot switch upper edge. These transducers control power and duration of actuation of the dislodgment mechanism and respectively include substantially circular coverings having indicia in the form of an upward pointing arrow and 'ON' and a downward pointing arrow and 'OFF' to identify the associated power and duration functions. Transducer 48 is disposed toward on upper right corner of the foot switch (e.g., as viewed in FIG. 4) and is actuated to increase the rate of the dislodgment mechanism. This transducer includes a substantially circular covering having indicia in the form of an upward pointing arrow to identify the associated mechanism rate function. Conversely, transducer 49 is disposed below transducer 48 and is actuated to decrease the dislodgment mechanism rate for the system. This transducer includes a substantially circular covering having indicia in the form of a downward pointing arrow to identify the associated mechanism rate function.

In addition, the foot switch may include a display 51 disposed toward the center of the foot switch within the confines of the foot switch transducers. Display 51 is preferably implemented by a conventional liquid crystal display (LCD), but maybe implemented by any other display devices (e.g., LED). The display typically includes a protective covering to prevent damage to the display during switch actuation, and may provide various information to a user concerning system operation (e.g., actual liquid temperature, desired temperature, dislodgment mechanism rate, current time, date, etc.). In this fashion, a user may control system operation via the foot switch and have information immediately available in response to foot switch actuation (e.g., the settings entered by the foot switch). Further, the foot switch may include transducers (not shown) that facilitate selective display of various information on displays 51 and/or 72. The foot switch components may be arranged in any fashion, however, a preferable arrangement enables manipulation of the transducers while providing an unobstructed view of display 51. It is to be understood that the foot switch may be configured to control any desired operational parameters or settings (e.g., duration of system or dislodgment mechanism operation, setting times for system or dislodgment mechanism operation, etc.) and may include any quantity or types of input devices to facilitate control of those settings.

The foot switch transducers are preferably implemented by force sensing resistors and associated circuitry. Specifically, each resistor is a relatively flat element with two terminals that essentially varies the resistance between the terminals in response to pressure applied in a direction substantially perpendicular to the plane of the element. The associated circuitry produces an output voltage based on the varying resistance, thereby providing a signals proportional to the pressure applied to the transducer. For examples of foot switches employing force sensing resistors, reference is made to U.S. Pat. No. 5,461,355 (Schemansky et al) and U.S. Pat. No. 5,712,460 (Carr et al), the disclosures of which are incorporated herein by reference in their entireties.

Figure 5:
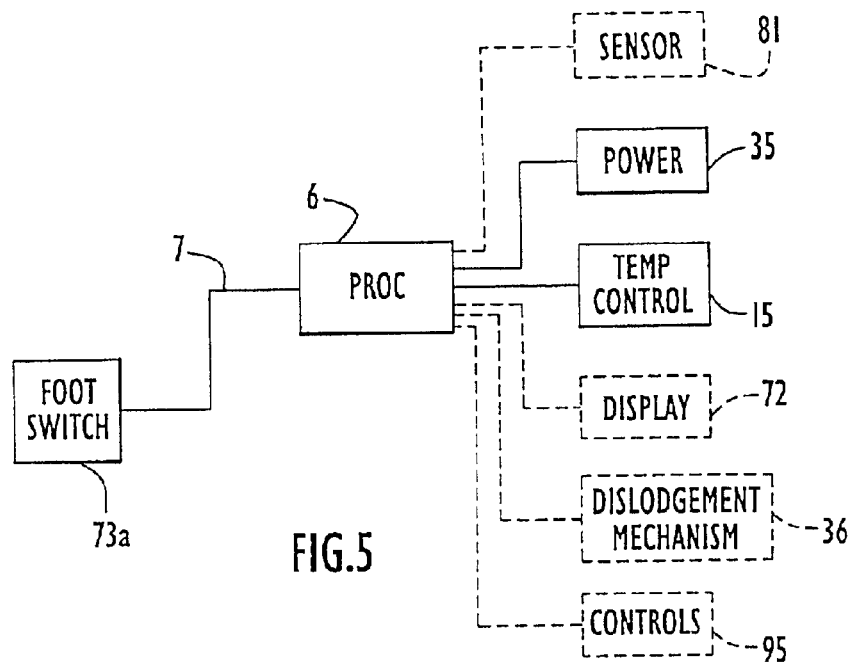
FIG. 5 is a schematic block diagram of exemplary circuitry for the system of FIG. 1 to control system operation in response to manipulation of the foot switch.

Thermal treatment 2a system receives the voltage signals from the foot switch and determines the appropriate actions as illustrated in FIG. 5. Specifically, system 2a includes a processor 6 disposed within cabinet 10 and coupled to foot switch 73a, power switch 35 and temperature control 15. The processor may further be coupled to dislodgment mechanism 36, display 72 and controls 95 when those devices are employed by the system, and may be implemented by any conventional microprocessor or other processing system or circuitry. In response to manipulation of foot switch 73a, processor 6 receives transducer signals via cable 7 indicating pressure applied to foot switch transducers. These signals are generally analog signals and are converted to digital signals compatible with the processor by an analog-to-digital converter (not shown) disposed either within the foot switch or within the thermal treatment system. Signals generated by the individual transducers may be memory mapped (e.g., placed in certain memory locations), may trigger particular processor interrupts or may utilize specific processor data lines to enable the processor to identify the transducers producing the signals.

The processor compares the transducer signals to corresponding transducer thresholds to determine the presence of transducer actuation (e.g., when the pressure applied to a transducer exceeds a threshold, the transducer is determined to be actuated). When a transducer is determined to be actuated, the processor controls the appropriate system components to perform the function associated with the actuated transducer. For example, in response to determining actuation of transducer 46 (FIG. 4), processor 6 toggles power switch 35 to alternately enable and disable power to the system. When transducer 41 is actuated, processor 6 controls temperature control 15 to increment or increase the system temperature setting. The incremental setting may be displayed on displays 51 and/or 72 to enable a user to view the incremental setting and manipulate foot switch transducers 41, 44 to achieve a desired temperature value. Similarly, actuation of transducer 44 causes the processor to control temperature control 15 to decrement or decrease the system temperature setting, while the decremental settings may be displayed on displays 51 and/or 72. The users ceases transducer actuation in response to a display of the desired temperature value. Further, actuation of transducer 45 causes processor 6 to enable a dislodgment mechanism power switch and increment the duration or time interval of mechanism operation. Conversely, manipulation of transducer 52 causes the processor to decrement the duration and disable mechanism power when the duration is decremented to a value indicating expiration of the time interval. Transducers 45, 52 operate in a manner similar to temperature transducers 41, 44 described above and are actuated until a desired duration is displayed. The rate of the dislodgment mechanism is controlled by transducers 48, 49 that operate in a manner similar to that described above for temperature transducers 41, 44. The dislodgment mechanism rate may be displayed on displays 51 and/or 72 with transducer 48 incrementing the setting and transducer 49 decrementing the setting. The mechanism rate transducers are basically actuated until a desired setting appears on displays 51 and/or 72. The processor maintains and displays the remaining time within the mechanism operating interval on displays 51 and/or 72 and controls the mechanism rate in accordance with the entered setting.

In addition, the processor may be further coupled to temperature sensor 81 disposed proximate basin 11 (FIG. 2) to measure the temperature of the sterile liquid as described above. The processor receives a signal from the temperature sensor indicating the measured temperature and processes that signal to display the measured temperature. The transducers associated with the display may be actuated to control processor 6 to display desired information on display 72. Cable 7 may further transfer information between the processor and foot switch to display the desired information on display 51. It is to be understood that the processor may control system operation in a manner similar to that described above for temperature control 15 and/or foot switch 73a in response to commands and/or system parameters entered via controls 95.

Operation of thermal treatment system 2a with foot actuated switch 73a is described with reference to FIGS. 1–5. Specifically, sterile drape 17a is placed over thermal treatment system 2a and within basin 11 to form a drape receptacle. A sterile medium or liquid is placed within the drape receptacle for cooling and/or forming surgical slush. The system may be manually controlled via power switch 35 and temperature control 15 and/or controls 95, but is preferably controlled by manipulation of foot switch 73a. The user actuates appropriate foot switch transducers to control system operation. For example, a user may actuate transducer 46 to initiate power, and further actuate transducers 41, 44 to enter a desired temperature setting as described above. In addition, transducers 45, 48, 49 and 52 may be actuated to control dislodgment mechanism operation as described above. The foot switch transfers transducer signals to the thermal treatment system where processor 6 determines transducer actuation and controls appropriate system components to perform the commanded actions as described above. The liquid temperature and other information may be selectively displayed on displays 51 and/or 72 in accordance with manipulation of the display transducers and/or controls 95. System operation may be controlled manually (e.g., via power switch 35 and temperature control 15 and/or controls 95) or via foot switch 73a, either individually or in any desired combination.

Figure 6:
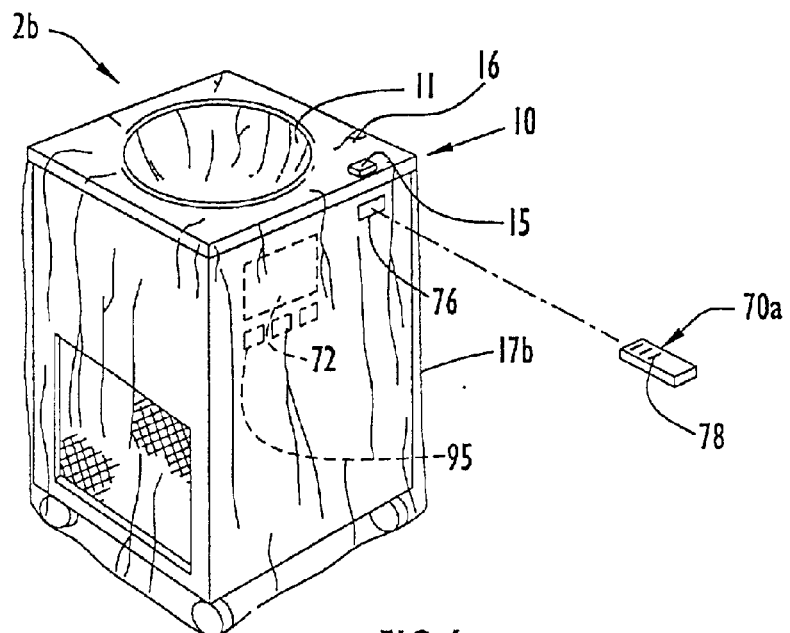
FIG. 6 is a view in perspective of a thermal treatment system for generating and collecting surgical slush having a surgical drape placed thereon and a remote control unit for controlling system operation remotely according to the present invention.
Figure 8:
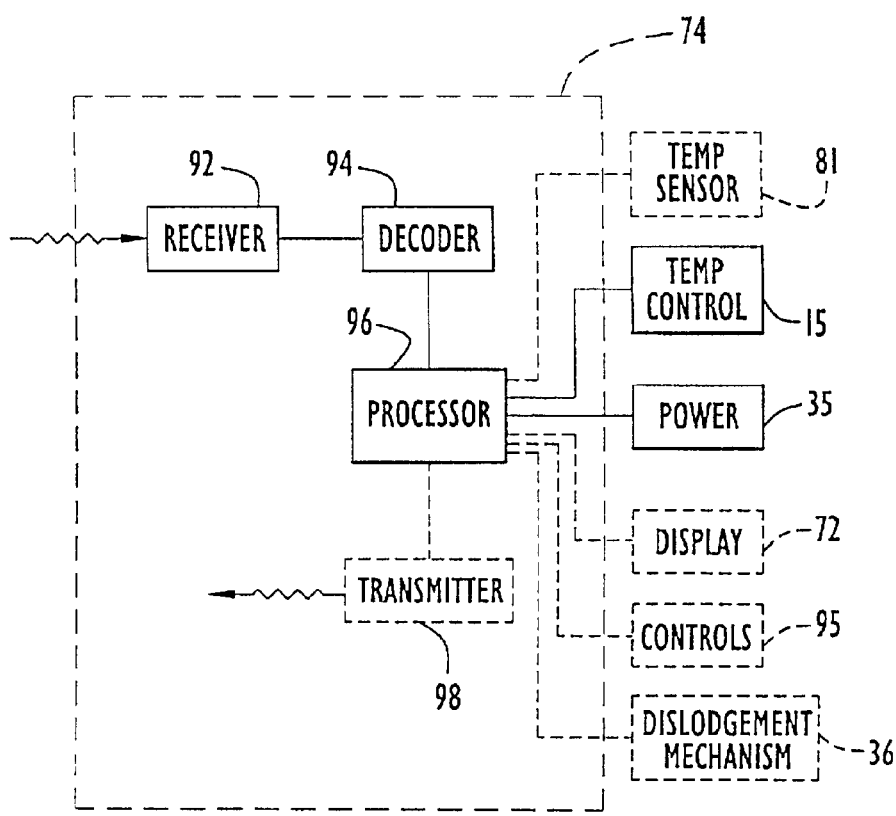
FIG. 8 is a schematic block diagram of an exemplary control circuit for the system of FIG. 6 to control system operation in response to transmitted controls from the remote control unit.
Figure 7:
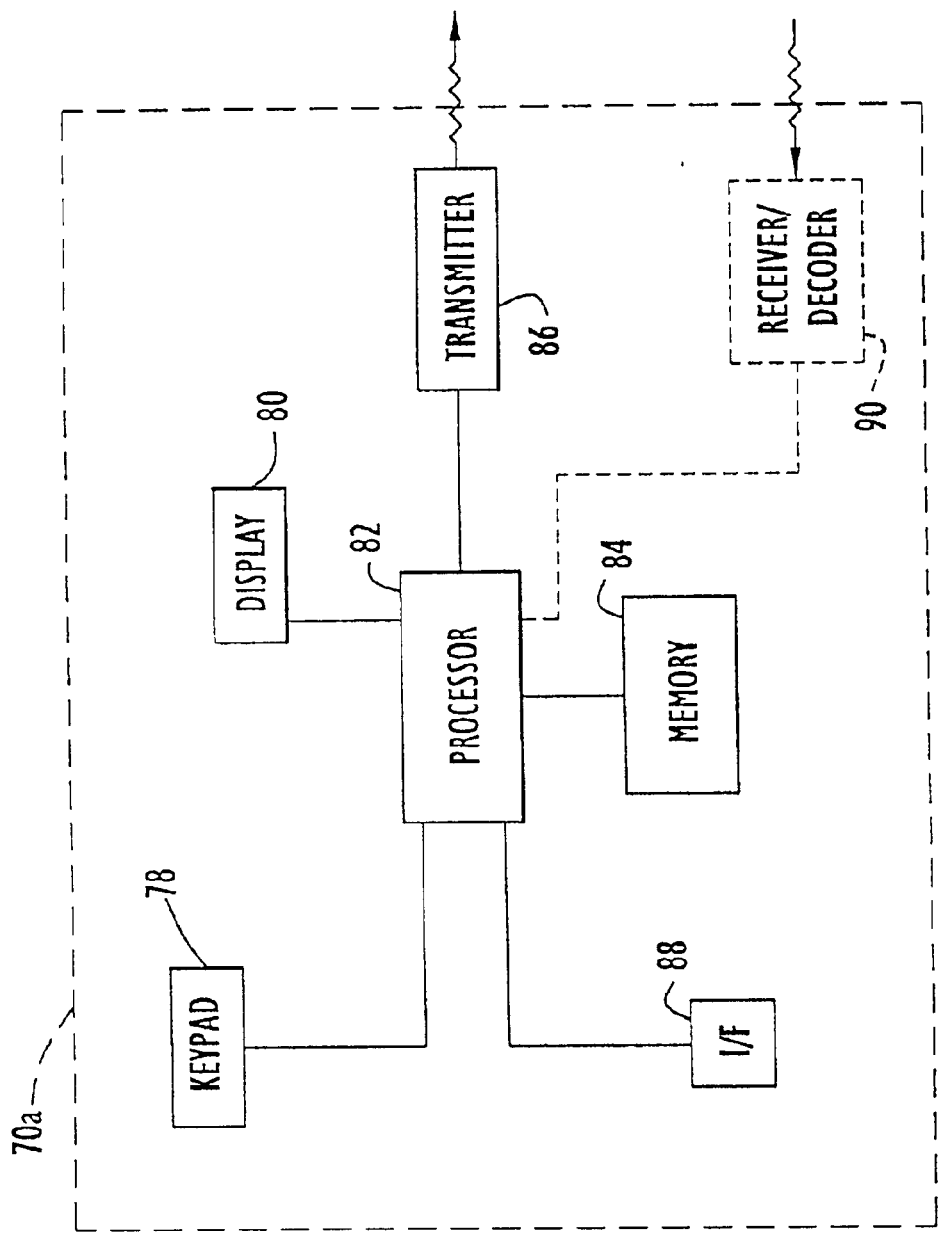
FIG. 7 is a schematic block diagram of an exemplary configuration for the remote control unit of FIG. 6.

In order to further enable sterile and non-sterile personnel to operate the thermal treatment system, the system may be controlled by a remote control unit as illustrated in FIGS. 6–8. Specifically, thermal treatment system 2b is substantially similar to system 2a described above, but includes a remote control unit 70a and control circuitry 74 (FIG. 8). A sterile drape 17b is placed over the system and within basin 11 to form a drape receptacle as described above. The drape is substantially similar to drape 17a described above, but is constructed of materials permitting signals from remote control unit 70a to pass therethrough and control system operation. Display 72 may be disposed on a side wall of cabinet 10 as described above, while controls 95 may be disposed below the display to facilitate selective display of and/or enter desired information. The display has dimensions sufficient to enable displayed information (e.g., operating status, desired temperature, actual liquid temperature, time, date, dislodgment mechanism period /activation, etc.) to be perceived through drape 17b by users located within extended ranges (e.g., distances extending to ten or more feet) from the system. A substantially rectangular window 76 is defined within a cabinet side wall below temperature control 15, and typically includes a substantially transparent covering constructed of materials that permit signals emitted from remote control unit 70a to pass therethrough. Control circuitry 74 is disposed coincident window 76 to receive the transmitted signals and control system operation in accordance with commands embedded within the signals as described below.

Referring to FIG. 7, remote control unit 70a typically has dimensions suitable for hand-held operation, and may be of the types disclosed in U.S. Pat. No. 4,264,982 (Sakarya), U.S. Pat. No. 4,825,200 (Evans et al), U.S. Pat. No. 4,866,434 (Keenan) and U.S. Pat. No. 6,008,735 (Chiloyan et al). The disclosures of these patents are incorporated herein by reference in their entireties. Control unit 70a, by way of example only, includes a keypad 78, an optional display 80, a processor 82, a memory 84, a transmitter 86 and an external interface 88. Keypad 78 facilitates entry of data into the remote control unit and may include any types of buttons, keys, wheels, switches or other input devices (e.g., balls, bars, joystick, etc.). The keypad generally includes specialty keys (e.g., keys associated with a specific function, such as on/off, increase/decrease settings, etc.) and a series of numeric keys and is connected to and forwards the entered information to processor 82. Processor 82 may be implemented by any conventional processing unit or circuit, such as a microprocessor, and receives entered information from keypad 78. Memory 84 is connected to the processor and typically contains software and operation code sets for transmitting commands to system 2b (FIG. 6). The processor decodes the information entered via keypad 78 and retrieves the appropriate operation codes from memory 84 for transmission to system 2b by transmitter 86. Memory 84 may store codes to facilitate adjustment or control of various system parameters and functions (e.g., power, temperature setting increase/decrease, dislodgment mechanism power duration, dislodgment mechanism rate increase/decrease, display of settings or measured temperature, or any other system parameter or function). Display 80 is preferably implemented by a liquid crystal display (LCD) and displays various information (e.g., date, time, liquid temperature, desired temperature, etc.) in response to processor control and display commands entered via keypad 78.

Transmitter 86 is connected to processor 82 and emits encoded command signals for processing by control circuitry 74 of system 2b. The transmitter may be implemented by any conventional or other transmitter, and may transmit any type of energy (e.g., infrared, RF, ultrasonic, visible light, etc.) capable of traversing the drape material. Interface 88 is connected to processor 82 and provides communication between the remote control unit and an external device, such as a computer. This permits additional information, such as command codes, to be transferred to and stored within the remote control unit. The interface may be implemented by any standard interface, such as RS-232.

A receiver/decoder 90 may further be incorporated into the remote control unit to receive information transmitted from system 2b as described below. Receiver 90 is preferably implemented by a conventional receiver/decoder and connected to processor 82 for receiving signals emitted from the system. These signals may include various types of information relating to system operation or the sterile liquid (e.g., status, liquid temperature, etc.). The receiver decodes the received signals and conveys the information to processor 82 for selective display on display 80 in accordance with display commands entered via keypad 78. Thus, a user may remotely monitor the system via the information displayed by the remote control unit. Information may be selectively displayed on displays 72 and/or 80 in accordance with display commands entered via keypad 78 or controls 95. In order to maintain the sterile field, the remote control unit may be sterilized or encased in a disposable sterile liner prior to use in each procedure.

Remote control unit 70a emits command signals to system 2b, while control circuitry 74 embedded within the system receives the signals and controls system operation in accordance with the received commands. Referring to FIG.

8, control circuitry 74 includes a receiver 92, a decoder 94 and a processor 96. Receiver 92 receives encoded signals emitted from remote control unit 70a through window 76 (FIG. 6). The receiver is preferably implemented by a conventional receiver compatible with transmitter 86, and conveys the encoded signals to decoder 94. The decoder decodes the received signals and forwards the decoded command signals to processor 96 for processing. The decoder may be implemented by any conventional decoders compatible with the signal encoder. Processor 96 may be implemented by any conventional processor or circuitry, and determines the command based on the transmitted operation code to control system operation.

The processor is typically connected to temperature control 15 and power switch 35, but may be further coupled to temperature sensor 81, display 72, controls 95 and dislodgment mechanism 36 (e.g., when the optional controls, display and dislodgment mechanism are employed by system 2b). The processor enables performance of various functions in accordance with commands transmitted from remote control unit 70a. For example, the processor may toggle power switch 35 to alternately enable and disable power to the system in response to a transmitted power or on/off command; control temperature control 15 to thermally treat the sterile liquid to an entered temperature; or control the rate or duration of dislodgment mechanism 36 in response to commands transmitted by the remote control unit. The desired temperature and mechanism rate and duration parameters may be directly entered via numeric keys of keypad 78. Alternatively, these settings may be entered via increment and decrement keys of keypad 78 with the entered setting being displayed on displays 72 and/or 80. Basically, the increment and decrement keys are manipulated until the desired setting appears on displays 72 and/or 80. Processor 96 maintains and displays the remaining time within a dislodgment mechanism operating interval on displays 72 and/or 80 and controls the mechanism rate in accordance with the entered setting. Further, the temperature measured by temperature sensor 81 may be provided to processor 96 for display on displays 72 and/or 80 along with various types of other information (e.g., time, date, desired temperature, dislodgment mechanism rate and/or duration, etc.) in accordance with display commands entered by the user via keypad 78 or controls 95.

In addition, control circuitry 74 may include a transmitter 98 to provide information to remote control unit 70a for display to a user on display 80 as described above. Transmitter 98 is similar to transmitter 86 of remote control unit 70a and is preferably implemented by a conventional transmitter compatible with the remote control unit receiver. The transmitter provides encoded signals conveying various information (e.g., actual temperature, mechanism duration, status, etc.) to the remote control unit for selective display on display 80 in accordance with display commands entered via keypad 78 as described above. It is to be understood that the remote control unit and control circuitry may be configured to control any desired operational parameters or settings. Further, processor 96 may control system operation in a similar manner to that described above for temperature control 15 and/or remote control unit 70a in response to commands and/or system parameters entered via controls 95.

Operation of remote controlled thermal treatment system 2b is described with reference to FIGS. 6–8. Specifically, sterile drape 17b is placed over system 2b and within basin 11 to form a drape receptacle. A sterile medium or liquid is placed within the drape receptacle for cooling and/or forming surgical slush. The system may be manually controlled via power switch 35 and temperature control 15 and/or controls 95, but is preferably controlled by operation of remote control unit 70a, The user depresses appropriate devices on keypad 78 to control system operation. For example, a user may initially enter "power on" commands followed by desired temperatures to initiate system operation. The remote control unit processes the keypad entries and retrieves the appropriate operation codes from memory for transmission to system 2b in the form of encoded signals as described above. Control circuitry 74 within the system receives and decodes the transmitted signals, and controls the appropriate system components to perform the actions indicated by the operation codes. The liquid temperature and other information is selectively displayed on displays 72 and/or 80 in accordance with display commands entered via keypad 78 or controls 95. System operation may be controlled manually (e.g., via power switch 35 and temperature control 15 and/or controls 95) and/or via remote control unit 70a, either individually or in any desired combination.

A thermal treatment system operable by sterile and non-sterile personnel to heat a sterile medium or liquid according to the present invention is illustrated in FIG. 9. Specifically, system 3a includes a cabinet or housing 31 and a warming basin 43 recessed into a top surface 34 of cabinet 31. Basin 43 may be of any shape, however, by way of example only, the basin is substantially rectangular. A heater power switch 47 and a temperature controller/indicator 38 are provided on top surface 34 adjacent the warming basin, while a foot actuated switch 73b is attached to the cabinet and may control system operation along with the power switch and controller/indicator as described below. Sterile surgical drape 17a, substantially similar to the drape described above for FIG. 1, is typically disposed over the system and within basin 43 to form a drape receptacle and contain a sterile medium within the basin in substantially the same manner described above for thermal treatment system 2a. The power switch and controller are adjustable manually through the drape to control system operation. The sterile liquid is substantially the same liquid described above to produce sterile slush and is warmed within the basin to produce a warmed sterile liquid. Display 72 may be disposed on a cabinet front wall, while display controls 95 may be disposed below the display to facilitate selective display of and/or enter desired information as described above. The display has dimensions sufficient to enable displayed information to be perceived through the drape by users located within extended ranges (e.g., distances extending to ten or more feet) from the system.

The manner of heating sterile liquid in warming basin 43 is illustrated schematically in FIG. 10. Specifically, an electrical circuit includes a power source 61 connected in series with a temperature control unit 62, a heater element or pad 60, and power control switch 47. Heater 60 is typically a thin wafer-like member disposed along the bottom surface of heating basin 43, secured to the basin by a suitable pressure sensitive adhesive having efficient heat transfer characteristics. Heater 60 has smaller dimensions than the basin bottom and is disposed at the approximate center of the bottom surface of the basin. The heater, for example, may be of the type described in the aforementioned Templeton patent. Temperature control unit 62 includes a device for adjusting current passing through the heating element 60 so as to permit selective adjustment of the heat applied to the liquid in basin 43. The power switch 47 permits selective application and removal of current flow with respect to heater 60.

A temperature sensor 64 is disposed adjacent basin 43 to sense the temperature of the liquid therein. Sensor 64 is connected in series with a voltage source 65 and an indicator 66. Voltage source 65 and power source 61 may be the same source, or the voltage for one may be derived from the other. Indicator 66 measures the current through temperature sensor 64, that current being proportional to the sensed temperature. Indicator 66 and temperature controller 62 may correspond, for example, to the temperature controller/indicator 38 described above. For further examples of heating unit operation, reference is made to the Faries, Jr. et al (e.g., U.S. Pat. Nos. 5,333,326; 5,429,801; 5,522,095; 5,524,643; 5,615,423; 5,653,938; 5,816,252; 5,857,467; 5,862,672 and 5,879,621) and other above-mentioned patents.

Figure 11:
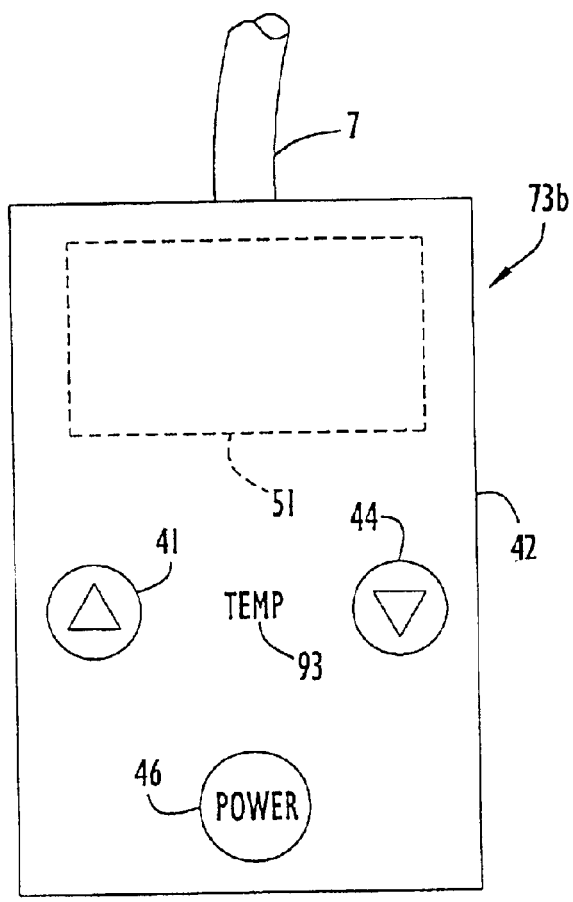
FIG. 11 is a top view in plan of an exemplary foot actuated switch for the system of FIG. 9.

The warming system may be controlled manually during a medical procedure by sterile personnel via power switch 47 and temperature controller 38 and/or controls 95, or remotely by sterile or non-sterile personnel via foot actuated switch 73b as illustrated, by way of example only, in FIG. 11. Specifically, foot switch 73b is similar to foot switch 73a described above and is coupled to system 3a via cable 7 that transfers information between the foot switch and system as described above. The foot switch includes a substantially rectangular housing 42 and several force sensitive transducers 41, 44 and 46 that detect switch actuation by the user as described below. The housing is constructed of suitably rigid materials to withstand pressure applied by the user during actuation, and may include various indicia 93 to identify functions associated with the transducers.

Transducers 41, 44, 46 typically include substantially circular coverings having indicia to identify the particular function associated with that transducer. By way of example only, transducer 41 is disposed toward the center of the foot switch left side edge (e.g., as viewed in FIG. 11) and is actuated to increase the system temperature setting as described above. This transducer includes a covering having indicia in the form of an upward pointing arrow to identify the associated function. Conversely, transducer 44 is disposed toward the center of the foot switch right side edge (e.g., as viewed in FIG. 11) and is actuated to decrease the system temperature setting. This transducer includes a covering having indicia in the form of a downward pointing arrow to identify the associated function. System power may be controlled by transducer 46 disposed toward the center of the foot switch lower edge. This transducer includes a covering having indicia in the form of 'POWER' to indicate the associated function.

In addition, the foot switch may include display 51 as described above and disposed toward and along the foot switch upper edge. The display typically includes a protective covering to prevent damage to the display during switch actuation, and may provide various information to a user concerning system operation as described above. Further, the foot switch may include transducers (not shown) that facilitate selective display of various information on displays 51 and/or 72 as described above. The foot switch transducers are substantially similar to and function in substantially the same manner as the corresponding transducers described above for foot switch 73a. The foot switch components may be arranged in any fashion, however, a preferable arrangement enables manipulation of the transducers while providing an unobstructed view of display 51. It is to be understood that the foot switch may be configured to control any desired operational parameters or settings (e.g., duration of system operation, setting actual times for system operation, etc.) and may include any quantity or types of input devices to facilitate control of those settings.

Figure 12:
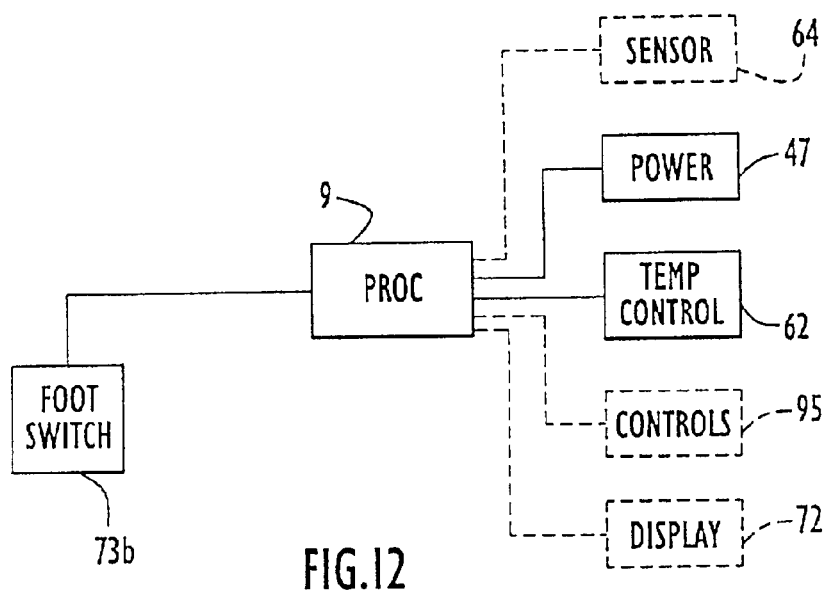
FIG. 12 is a schematic block diagram of exemplary circuitry for the system of FIG. 9 to control system operation in response to manipulation of the foot switch.

System 3a receives signals from the foot switch and determines the appropriate actions as illustrated in FIG. 12. Specifically, system 3a includes a processor 9 disposed within cabinet 31 and coupled to foot switch 73b, power switch 47 and temperature controller 62. The processor may further be coupled to display 72 and controls 95 when those devices are employed by the system. The processor is substantially similar to processor 6 described above and may be implemented by any conventional microprocessor or other processing system or circuitry. In response to manipulation of foot switch 73b, processor 9 receives transducer signals via cable 7 indicating pressure applied to foot switch transducers. These 46 signals are generally analog signals and are converted to digital signals compatible with the processor via an analog-to-digital converter (not shown) disposed either within the foot switch or within system 3a. Processor 9 generally employs the memory mapping, interrupt or specific data line techniques described above to identify the transducers producing the signals.

Processor 9 compares the transducer signals to corresponding transducer thresholds as described above to determine the transducers actuated by the user. When a transducer is determined to be actuated, the processor controls the appropriate system components to perform the function associated with the actuated transducer. For example, in response to determining actuation of transducer 46, processor 9 toggles power switch 47 to alternately enable and disable power to the system. When transducer 41 is actuated, the processor controls temperature controller 62 to increment the system temperature setting. The incremental setting may be displayed on displays 51 and/or 72 to enable a user to view the incremental setting and manipulate foot switch transducers 41, 44 to achieve a desired temperature value. Similarly, actuation of transducer 44 causes the processor to control temperature controller 62 to decrement or decrease the temperature setting, while the decremental setting may be displayed on displays 51 and/or 72. The user ceases transducer manipulation in response to display of the desired temperature value.

In addition, the processor may be further coupled to temperature sensor 64 disposed proximate basin 43 (FIG. 10) to measure temperature of the sterile liquid as described above. The processor receives a signal from the temperature sensor indicating the measured liquid temperature and processes that signal to display the measured temperature. The transducers associated with the display may be actuated to control processor 9 to display desired information on display 72. Cable 7 may further transfer information between the processor and foot switch to display the desired information on display 51. It is to be understood that the processor may control system operation in a manner similar to that described above for temperature control 38 and/or foot switch 73b in response to commands and/or system parameters entered via controls 95.

Operation of warming system 3a with foot actuated switch 73b is described with reference to FIGS. 9–12. Specifically, sterile drape 17a is placed over system 3a and within basin 43 to form a drape receptacle as described above. A sterile medium or liquid is placed within the drape receptacle for heating to produce a warmed sterile liquid. The warming system may be manually controlled via power switch 47 and temperature control 38 and/or, controls 95, but is preferably controlled by manipulation of foot switch 73b. The user actuates appropriate foot switch transducers to control system operation. For example, a user may actuate transducer 46 to initiate system power, and further actuate transducers 41, 44 to set a desired temperature as described above. The foot switch transfers transducer signals to the warming system where processor 9 determines transducer actuation and controls appropriate system components to perform the commanded actions as described above. The liquid temperature and other information may be selectively displayed on displays 51 and/or 72 in accordance with manipulation of the display transducers and/or controls 95. System operation may be controlled manually (e.g., via power switch 47 and temperature control 38 and/or controls 95) or via foot switch 73b, either individually or in any desired combination.

Figure 14:
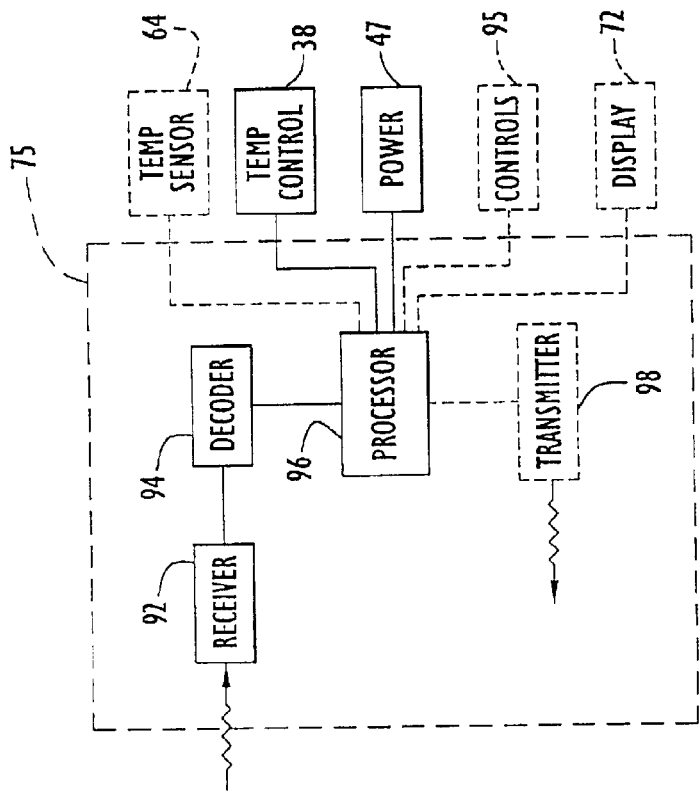
FIG. 14 is a schematic block diagram of an exemplary control circuit for the system of FIG. 13 to control system operation in response to transmitted controls from the remote control unit.
Figure 13:
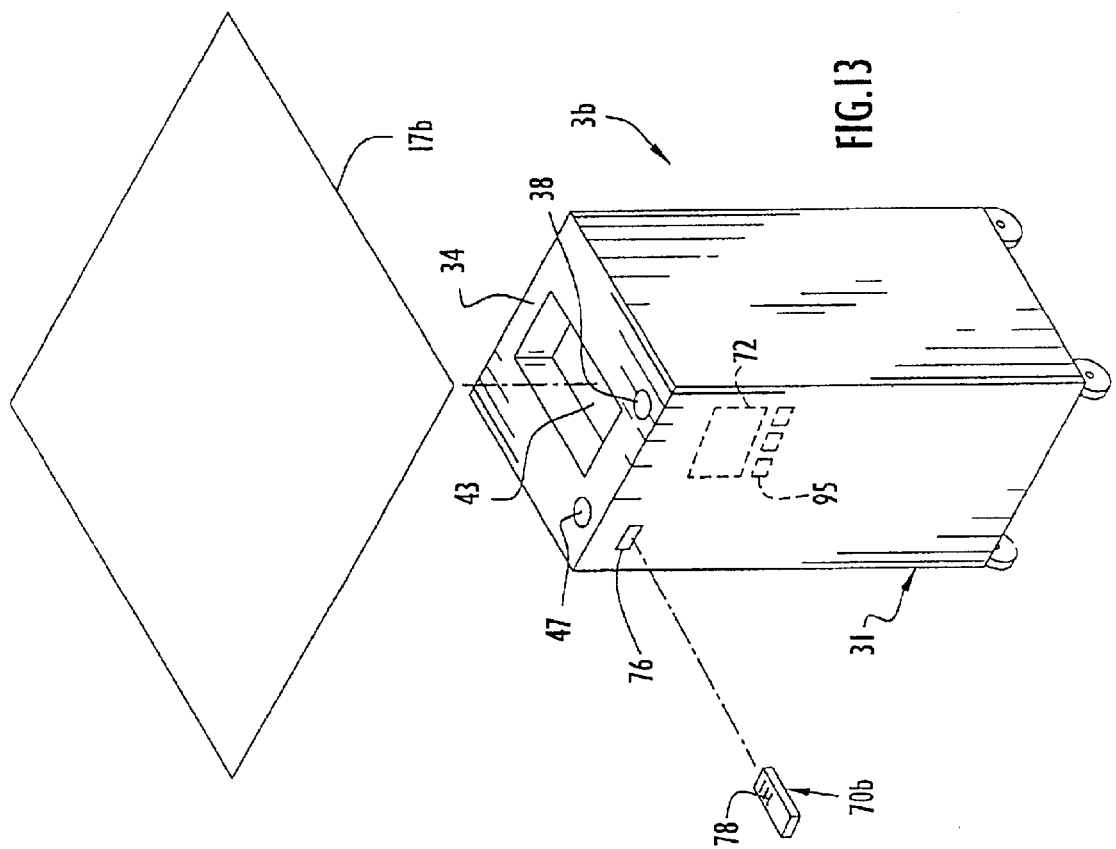
FIG. 13 is an exploded view in perspective of a thermal treatment system for warming a sterile medium having a surgical drape for placement thereon and a remote control unit for controlling system operation remotely according to the present invention.

A remote controlled thermal treatment system operable during a medical procedure by sterile or non-sterile personnel for warming a sterile medium according to the present invention is illustrated in FIGS. 13–14. Specifically, warming system 3b is substantially similar to warming system 3a described above, but includes remote control unit 70b and control circuitry 75 (FIG. 14). A drape 17b, substantially similar to the drape described above for system 2b, is placed over the system and within basin 43 to form a drape receptacle as described above. Drape 17b is constructed of materials permitting signals from remote control unit 70b to pass therethrough and control system operation. Display 72 may be disposed on the cabinet front wall below temperature control 38, while controls 95 may be disposed below the display to facilitate selective display of and/or enter desired information. display has dimensions sufficient to enable displayed information (e.g., operating status, desired temperature, actual liquid temperature, time, date, etc.) to be perceived through drape 17b by users located within extended ranges (e.g., distances extending to ten or more feet) from the system. Substantially rectangular window 76 is defined within the cabinet front wall below power switch 47, and typically includes a substantially transparent covering constructed of materials that permit signals emitted from remote control unit 70b to pass therethrough. Control circuitry 75 is disposed coincident window 76 to receive the transmitted signals and control system operation in accordance with commands embedded within the signals as described below.

Remote control unit 70b emits command signals to warming system 3b to control system operation and is substantially similar to remote control 70a described above for FIG. 7, except that remote control unit 70b stores and transmits operation codes corresponding to warming system operations (e.g., power, temperature setting increase/decrease, etc.). In order to maintain the sterile field, the remote control unit may be sterilized or encased in a sterile disposable liner prior to each procedure as described above. Control circuitry. 75 is substantially similar to circuitry 74 described above and is embedded within cabinet 31 to control system operation in accordance with commands received from remote control unit 70b. Referring to FIG. 14, control circuitry 75 includes receiver 92, decoder 94 and processor 96, each as described above. Receiver 92 receives signals emitted from remote control unit 70b through window 76 (FIG. 13) and conveys the encoded signals to decoder 94 as described above. The decoder decodes the received signals and forwards the decoded signals to processor 96 for processing as described above. Processor 96 determines the command based on the transmitted operation code to control system operation.

The processor is typically connected to temperature control 38 and power switch 47, but may be further coupled to temperature sensor 64, display 72 and controls 95 (e.g., when the optional display and controls are employed by the system). The processor enables performance of various functions in accordance with commands transmitted from remote control unit 70b. For example, the processor may toggle power switch 47 to alternately enable and disable power to the system in response to a transmitted power or on/off command, or control temperature control 38 to thermally treat the sterile medium to an entered temperature in response to a corresponding command transmitted by the remote control unit. The desired temperature may be directly entered via numeric keys of keypad 78 or entered via increment and/or decrement keys of the keypad as described above. Further, the temperature measured by temperature sensor 64 may be provided to processor 96 for display on displays 72 and/or 80 along with various types of other information (e.g., time, date, desired temperature, etc.) in accordance with display commands entered by the user via keypad 78 or controls 95.

In addition, control circuitry 75 may include transmitter 98 to provide information to remote control unit 70b for display to a user on display 80 as described above. Transmitter 98 provides encoded signals conveying various information (e.g., actual and desired temperatures, status, etc.) to the remote control unit for selective display on display 80 (FIG. 7) in accordance with display commands entered via keypad 78. It is to be understood that the remote control unit and control circuitry may be configured to control any desired operational parameters or settings. Further, processor 96 may control system operation in a similar manner to that described above for temperature control 38 and/or remote control unit 70b in response to commands and/or system parameters entered via controls 95.

Operation of remote controlled thermal treatment system 3b is described with reference to FIGS. 13–14. Specifically, sterile drape 17b is placed over cabinet 31 and within basin 43 to form a drape receptacle as described above. A sterile medium or liquid is placed within the drape receptacle for heating to produce a warmed sterile liquid. The system may be manually controlled via power switch 47 and temperature control 38 and/or controls 95, but is preferably controlled by operation of remote control unit 70 b. The user depresses appropriate devices or keys on keypad 78 to control system operation. For example, a user may initially enter "power on" commands followed by desired temperatures to initiate system operation. Remote control unit 70 b processes keypad entries and retrieves the appropriate operation codes from memory for transmission to system 3b in the form of encoded signals as described above. Control circuitry 75 within the system receives and decodes the transmitted signals, and controls the appropriate system components to perform the actions indicated by the operation codes. The liquid temperature and other information is selectively displayed on displays 72 and/or 80 in accordance with display commands entered via keypad 78 or controls 95. System operation may be controlled manually (e.g., via power switch 47 and temperature control 38 and/or controls 95) and/or via remote control unit 70 b, either individually or in any desired combination.

Figure 15:
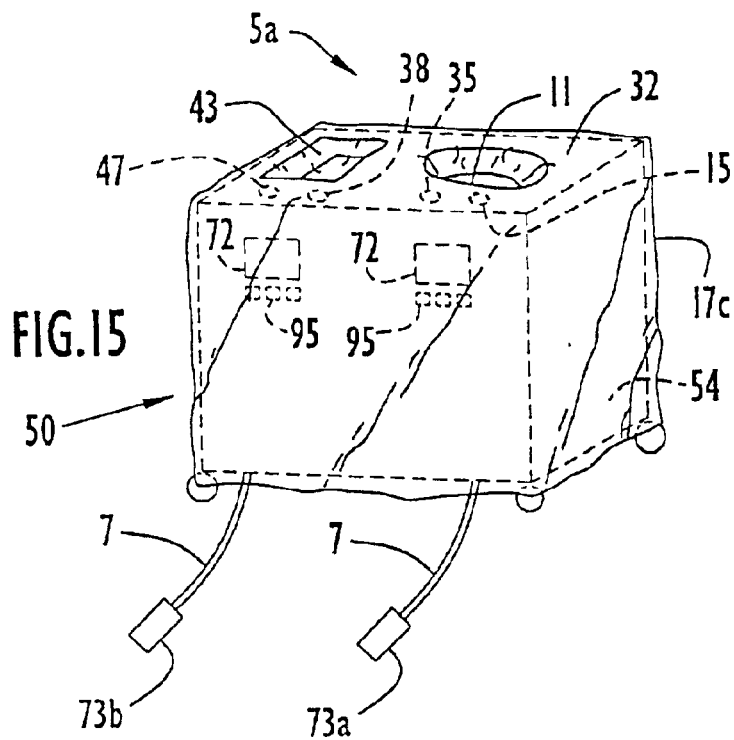
FIG. 15 is a view in perspective of a plural basin thermal treatment system having a surgical drape placed thereon and foot actuated switches to control system operation according to the present invention.

A plural basin thermal treatment system operable during a medical procedure by sterile or non-sterile personnel to thermally treat a sterile medium according to the present invention is illustrated in FIG. 15. Specifically, a thermal treatment system 5a has an integral assembly 50 including basin 11 for cooling a sterile medium or liquid and basin 43 for heating sterile liquid, each recessed into top surface 32 of a common cabinet 54. The thermal treatment system basins provide for simultaneous cooling and heating of a sterile medium. Also disposed in top surface 32 are cooling unit power switch 35, cooling unit temperature control 15, heater power switch 47 and a heater temperature control 38. The cooling and heating basins are substantially similar to and function in substantially the same manner as the basins of the cooling and warming systems described above. For further examples of the structure and operation of integral assembly 50, reference is made to the aforementioned Faries, Jr. et al patents (e.g., U.S. Pat. Nos. 5,333,326; 5,429,801; 5,522,095; 5,524,643; 5,615,423; 5,653,938; 5,816,252; 5,857,467; 5,862,672 and 5,879,621).

A sterile drape 17c for use with the plural basin system is substantially similar to drape 17a described above, but is of sufficient size to encompass basins 11 and 43. The drape is placed over the system and within basins 11, 43 to form drape receptacles within the basins as described above. Displays 72 may each be disposed on an assembly front wall below a respective basin, while controls 95 may be disposed beneath the respective displays to facilitate selective display of and/or enter desired information. The displays have dimensions sufficient to enable displayed information to be perceived through the drape by users located within extended ranges (e.g., distances extending to ten or more feet) from the system as described above. Power switches 35, 47, temperature controls 15, 38 and controls 95 are manually adjustable through drape 17c to control system operation. In addition, foot actuated switches 73a, 73b are attached to cabinet 54 to control system operation as described below. In particular, foot switch 73a is substantially similar to the foot switch described above for FIG. 4 and controls operation of cooling basin 11, while foot switch 73b is substantially similar to the foot switch described above for FIG. 8 and controls operation of warming basin 43. Foot switches 73a, 73b are each coupled to system 5a via respective cables 7 that each transfer information between a foot switch and system 5a.

Figure 16:
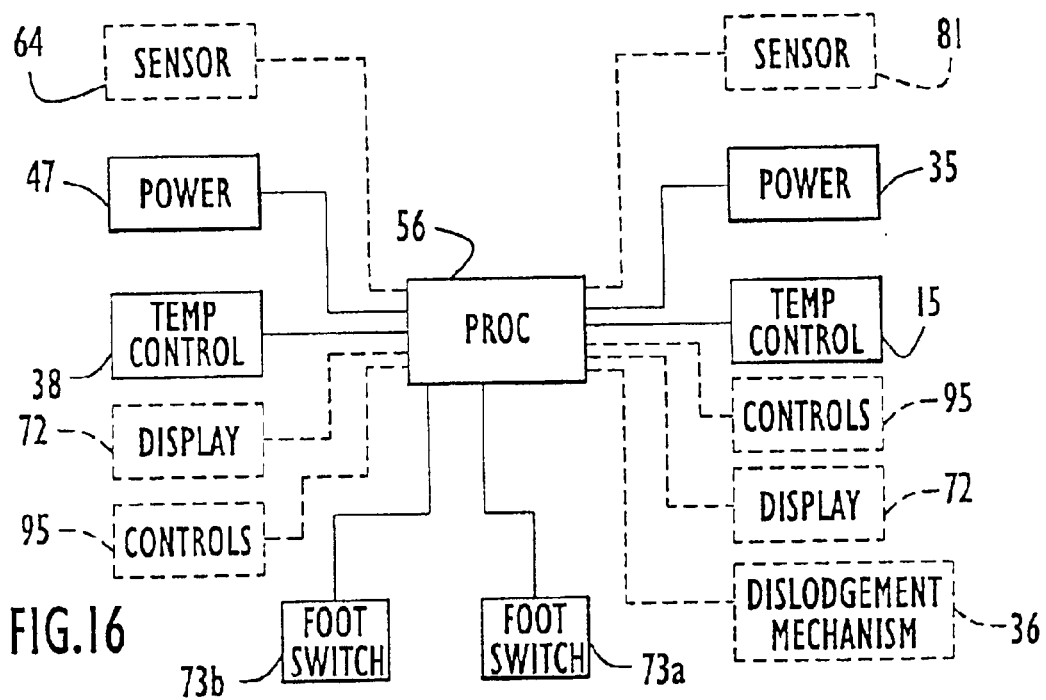
FIG. 16 is a schematic block diagram of exemplary circuitry for the system of FIG. 15 to control system operation in response to manipulation of the foot switches.

The foot switches each provide signals to system 5a to control system operation as illustrated in FIG. 16. Specifically, system 5a includes a processor 56 disposed within assembly 50 and coupled to foot switches 73a, 73b, power switches 35, 47 and temperature controls 15, 38. The processor may further be coupled to cooling basin dislodgment mechanism 36, displays 72 and controls 95 (e.g., when these optional devices are employed by the system) and may be implemented by any conventional microprocessor or other processing system or circuitry. In response to manipulation of foot switches 73a, 73b, processor 56 receives transducer signals from the foot switches via cables 7 indicating pressure applied to foot switch transducers. These signals are generally analog signals and are converted to digital signals compatible with the processor by an analog-to-digital converter (not shown) disposed either within each foot switch or within system 5a. Processor 56 generally employs the memory mapping, interrupt or specific data line techniques described above to identify the transducers producing the signals.

The processor compares the transducer signals to corresponding transducer thresholds to determine actuation of transducers as described above. When transducers are determined to be actuated, the processor controls the appropriate system components to perform the functions associated with the actuated transducers for the respective basins in substantially the same manner described above. In addition, the processor may be further coupled to temperature sensors 64, 81 (FIGS. 2 and 10) and receive signals from these sensors indicating the measured temperature of liquid within basins 11, 43. The processor processes the signals to display the measured temperatures on respective displays 72. The transducers associated with the respective displays may be actuated to control processor 56 to display desired information on displays 72. Cables 7 may transfer information between the processor and foot switches to display the information on the foot switch displays as described above. It is to be understood that the processor may control system operation in a manner similar to that described above for temperature controls 15, 38 and foot switches 73a, 73b in response to commands and/or system parameters entered via respective controls 95.

Operation of the plural basin system with foot actuated switches 73a, 73b is described with reference to FIGS. 15–16. Specifically, sterile drape 17c is placed over system 5a and within each basin to form respective drape receptacles therein as described above. A sterile medium or liquid is placed within each drape receptacle for cooling or heating. Each basin may be manually controlled via associated power switches 35, 47 and temperature controls 15, 38 and/or controls 95, but is preferably controlled by manipulation of a corresponding foot switch 73a, 73b. The user actuates appropriate transducers of a foot switch to control an associated basin as described above. For example, a user may actuate transducer 46 of foot switch to 73a (FIG. 4) to initiate power to basin 11, and further actuate transducers 41, 44 to set a desired temperature for that basin as described above. Manipulation of transducers 41, 44 and 46 of foot-switch 73b (FIG. 8) provides similar control over basin 43. Transducers 45 and 52 of foot switch 73a may also be actuated to control a dislodgment mechanism of that basin as described above. Each foot switch transfers signals to system 5a where processor 56 determines transducer actuation and controls appropriate system components to perform the commanded actions as described above. The liquid temperature within each basin and other information may be selectively displayed on corresponding foot switch displays 51 and/or displays 72 in accordance with manipulation of the display transducers and/or controls 95 as described above. System operation may be controlled manually (e.g., via power switches 35, 47 and temperature controls 15, 38 and/or controls 95) or via foot switches 73a, 73b, either individually or in any combination.

A remote controlled plural basin thermal treatment system operable during a medical procedure by sterile or non-sterile personnel to thermally treat a sterile medium according to the present invention is illustrated in FIGS. 17–18. Specifically, thermal treatment system 5b is substantially similar to system 5a described above, but includes remote control unit 70c and control circuitry 77 (FIG. 18). A sterile drape 17d for use with system 5b is substantially similar to drape 17b described above, but is of sufficient size to encompass basins 11 and 43. The drape is placed over system 5b and within basins 11, 43 to form drape receptacles within the basins as described above. Displays 72 may be disposed on the cabinet front wall beneath an associated basin 11, 43, while controls 95 may be disposed beneath each of the respective displays to facilitate selective display of and/or enter desired information. The displays each have dimensions sufficient to enable displayed information to be perceived through drape 17d by users located within extended ranges (e.g., distances extending to ten or more feet) from the system. Substantially rectangular window 76 is defined within a substantially central section of the cabinet front wall toward the front wall upper edge, and typically includes a substantially transparent covering constructed of materials that permit signals emitted from remote control unit 70c to pass therethrough. Control circuitry 77 is disposed coincident window 76 to receive the transmitted signals and control system operation in accordance with commands embedded within the signals as described below.

Remote control unit 70c emits command signals to system 5b to control system operation and is substantially similar to remote control units 7a, 70 b described above, except that remote control unit 70c stores and transmits operation codes corresponding to both cooling and warming basins. The operation codes typically include information to identify the basin associated with the function. Control circuitry 77 is substantially similar to circuitry 74, 75 described above and is embedded within assembly 50 to control system operation in accordance with commands received from remote control unit 70c as illustrated in FIG. 18. Specifically, control circuitry 77 includes receiver 92, decoder 94 and processor 96, each as described above. Receiver 92 receives signals emitted from remote control unit 70c through window 76 (FIG. 17) and conveys the encoded signals to decoder 94 as described above. The decoder decodes the received signals and forwards the decoded signals to processor 96 for processing as described above. Processor 96 determines the command and corresponding basin based on the transmitted operation code to control system operation. A user typically enters into the remote control unit an identifier along with a command to indicate the basin being remotely controlled. The remote control unit processor receives the identifier and retrieves the appropriate operation code for the function containing basin information. System processor 96 receives the transmitted code and utilizes the basin information within the code to control the appropriate basin.

Processor 96 is typically coupled to power switches 35, 47 and temperature controls 15, 38, but may be further coupled to dislodgment mechanism 36, displays 72 and controls 95 (e.g., when these optional devices are employed by the system). The system components are controlled by the processor to perform various functions in accordance with the transmitted operation codes as described above. Further, processor 96 may be coupled to temperature sensors 64, 81 (FIGS. 2 and 10) and receive signals from these sensors indicating the measured temperature of liquid within basins 11, 43. The processor processes the signals to display the measured temperatures on displays 72 and/or 80. Further, the temperature measured by temperature sensors 64, 81 may be provided to processor 96 for display along with various types of other information (e.g., date, time, desired temperature, etc.) in accordance with display commands entered by the user via keypad 78 or controls 95.

In addition, control circuitry 77 may include transmitter 98 to provide information to remote control unit 70c for display to a user on display 80 as described above. The transmitter provides encoded signals conveying various information (e.g., actual and desired temperatures of the basins, basin status, etc.) to the remote control unit for selective display on display 80 (FIG. 7) in accordance with display commands entered via keypad 78. It is to be understood that the remote control unit and control circuitry may be configured to control any desired operational parameters or settings. Further, processor 96 may control system operation in a similar manner to that described above for temperature controls 15, 38 and/or remote control unit 70c in response to commands and/or system parameters entered for the basins via corresponding controls 95.

Operation of the remote controlled thermal treatment system is described with reference to FIGS. 17–18. Specifically, sterile drape 17d is placed over system 5b and within each basin to form drape receptacles therein as described above. A sterile medium or liquid is placed within each drape receptacle for cooling or heating. Each basin may be manually controlled via associated power switches 35, 47 and temperature controls 15, 38 and/or controls 95, but is preferably controlled by operation of remote control unit 70c. The user depresses appropriate devices on keypad 78 to control system operation as described above. The remote control unit processes the keypad entries and retrieves the appropriate operation codes (e.g., including a basin identifier as described above to designate the basin being controlled) from memory for transmission to system 5b in the form of encoded signals as described above. Control circuitry 77 within the system receives and decodes the transmitted signals, and controls the appropriate system components to perform the actions indicated by the operation codes. The liquid temperature and other information pertaining to the basins or system is selectively displayed on display 80 and/or respective displays 72 in accordance with display commands entered via keypad 78 or controls 95. System operation may be controlled manually (e.g., via power switches 35, 47 and temperature controls 15, 38 and/or controls 95) or via the remote control unit, either individually or in any desired combination.

It will be appreciated that the embodiments described above and illustrated in the drawings represent only a few of the many ways of implementing a remote controlled thermal treatment system and method for controlling the system remotely to thermally treat sterile surgical liquid.

The slush, warming and plural basin systems and their corresponding assembly or housings may be of any shape or size and may be constructed of any suitable materials. The plural basin system may include any quantity of heating and/or cooling basins in any combinations. The basins may be of any shape or size, and may be constructed of any suitable thermal conducting materials (e.g., stainless steel). The systems may include any conventional or other heating and/or refrigeration units to thermally treat the sterile medium or other substance to any desired temperature. The heating unit may include any conventional or other heating device and components to control heating of the basin to any desired temperature (e.g., preferably to temperatures near or above normal body temperature, such as temperatures in the approximate range of 95° F.–110° F. ). The cooling unit may include any conventional or other cooling or refrigeration device and components to control cooling of the basin to any desired temperature (e.g., preferably to temperatures near or below the freezing temperature of the sterile liquid or medium, such as temperatures in the approximate range of −32° F. to 32° F. ). The temperature sensors maybe implemented by any conventional or other temperature sensing device (e.g., infrared, RTD, etc.). The basins may be disposed in any arrangement or at any suitable locations on the systems. The systems may thermally treat (e.g. heat or cool) any type of medium or liquid, while the cooling basins may include any type of conventional or other dislodgement mechanism, such as those described above or in the aforementioned patents. The systems may include both the foot switches and remote control units, and may be operable manually (e.g., via the power switches and controls), via the foot switches or via the remote control units, either individually or in any desired combination. The foot switches and/or remote control units may be employed by any of the thermal treatment or slush systems described above or disclosed in the aforementioned patents in substantially the same manner described above. The systems may include any quantity or type (e.g., LED, LCD, etc.) of display of any shape or size to be perceived from any desired distances. The display may be disposed at any suitable locations, and may indicate any information, such as that relating to any system or medium characteristics or parameters (e.g., desired or actual medium temperature, operating interval, time, date, dislodgement mechanism rate, etc.). The controls (e.g., controls 95) may be of any quantity, shape or size, and may be implemented by any type of input device (e.g., keys, buttons, bars, joystick, ball, touch screen display, voice recognition, etc.). The controls may be disposed on the systems at any suitable locations, and facilitate entry and/or display of any type of information.

The drapes employed with the cooling, heating and plural basin systems may be of any size or shape, and may be constructed of any suitable materials. The drapes employed with the foot switch and remote control unit are preferably transparent or translucent to facilitate manipulation of controls through the drape, however, these drapes may have any degree of transparency (e.g., including opaque). The drapes employed with the remote control units may be constructed of any suitable materials enabling remote control unit signals to pass therethrough.

The foot actuated switches and housings may be of any shape or size, and may be constructed of any suitable materials. The foot switches may be manipulated by any portion of a user body. The foot switches may include any quantity of any type of input device to control system operation. The transducers may be arranged in any fashion and may be implemented by any type of conventional or other pressure sensing device (e.g., pressure sensitive resistors, electromechanical devices, etc.) and associated circuitry. The foot switches may include any quantity of any type of indicia to indicate specific functions. Further, the transducers may include any quantity or type of covering of any shape or size having any suitable indicia thereon describing the transducer function. The coverings may be constructed of any suitable materials. The foot switches may include any quantity or type (e.g., LED, LCD, etc.) of display of any shape or size disposed at any suitable locations. The display may include a protective covering of any shape or size and constructed of any suitable materials enabling viewing of the display therethrough. The display may indicate information relating to any system or medium characteristics or parameters (e.g., desired or actual medium temperature, operating interval, time, date, dislodgement mechanism rate, etc.). The foot switches may include transducers or other devices to control any operating parameter or system functions.

The plural basin system may alternatively include a single foot switch to control plural system basins, while the foot switches may employ wireless technology utilizing any type of energy (e.g., infrared, RF, visible light, ultrasound, etc.) to facilitate communication of control and other information with the system. The systems may employ any quantity of foot switches to control one or more basins. The system processors receiving data from the foot switches may be implemented by any conventional or other processor or circuitry. The transducer actuation thresholds may be set to any desired values to indicate actuation from any amount of applied pressure. The foot switches may interface the processors in any desired fashion to facilitate identification of transducers producing received signals (e.g., memory mapping, interrupts, specific line, transducer signals including identification information, etc.). The foot switch cables may be implemented by any type of conventional or other cable suitable for transferring information between the foot switches and systems. The cables and systems may include connectors to enable the foot switches to be compatible with and utilized by different systems. The foot switches may be detached from the housing and in communication with the system via wire or wireless technology, or may alternatively be attached to or mounted on the system housing to control system operation in substantially the same manner described above.

The remote control units and their housings may be of any shape or size and may be constructed of any suitable materials. The unit components (e.g., processor, transmitter, decoder, receiver/decoder, keypad, memory) may be implemented by any conventional or other components or circuitry capable of performing their functions. The keypad may include any quantity or types of input devices (e.g., keys, buttons, bars, wheels, touch screen, joystick, ball, etc.), and may include any alphanumeric or specialty keys. The units may include any quantity or type (e.g., LED, LCD, etc.) of display of any shape or size disposed at any suitable locations. The display may indicate information relating to any system or medium characteristics or parameters (e.g., desired or actual medium temperature, operating interval, time, date, dislodgement mechanism rate, etc.). The units may be configured to control any operating parameter or system functions. The units may control any quantity of basins, and may include any quantity or type of software and/or operation codes to control system parameters and operation. The codes may include any length or format, may utilize any type of alphanumeric or other characters or bit streams, and may contain any type of information (e.g., operation, parameter, basin identifier, machine identifier, etc.). Further, the units may be configured to be universal and for use with different machines. The units may encode signals in any desired format (e.g., including uncoded signals), and may transmit in the form of any type of wave or signal utilizing any type of energy (e.g., infrared, RF, visible light, ultrasound, etc.). The units may alternatively utilize a cable for communication with the systems.

The systems employing the remote control units may include control circuitry having components (e.g., receiver, decoder, transmitter, processor) implemented by any conventional or other components or circuitry performing those functions. The receiver and decoder may be implemented by any devices compatible with the unit transmitter, while the unit receiver/decoder may be implemented by any device compatible with the system transmitter. The transmitters may transmit any type of wave or signal utilizing any desired energy (e.g., infrared, RF, visible light, ultrasound, etc.) at any desired frequency. The remote units may be sterilized or encased in a sterile liner prior to each use in a sterile environment. The liner may be of any shape or size, and may be constructed of any suitable materials enabling signals from the remote control units to pass therethrough. The plural basin system may employ any quantity of remote control units to control basins individually (e.g., one unit for each basin). The system windows may be of any quantity, shape or size, and may include coverings of any shape or size and constructed of any suitable materials enabling signals from the remote control units to pass therethrough. Alternatively, the windows may be implemented without the coverings. The remote control units are typically portable and detached from the system housing, but may be removably attached to the housing (e.g., via a holder, bracket, etc.), and may control system operation from any desired distances.

The system and remote control unit processors may include software developed in any suitable computer language to perform the described functions. It is to be understood that one of ordinary skill in the computer arts could develop the software for the processors based on the functional descriptions contained herein. Further, the processors may be implemented by any hardware or circuitry to perform the described functions. The control circuitry of the systems may be implemented by any conventional or other devices or components arranged in any fashion to process the signals from the foot switches and remote control units and control system operation.

From the foregoing description it will be appreciated that the invention makes available a novel remote controlled thermal treatment system and method for controlling the system remotely to thermally treat sterile surgical liquid wherein a thermal treatment system is controlled via a foot actuated switch or remote control unit to thermally treat a sterile surgical liquid contained therein to desired temperatures.

Having described preferred embodiments of new and improved remote controlled thermal treatment system and method for controlling the system remotely to thermally treat sterile surgical liquid, it is believed that other modifications, variations and changes will be suggested to those skilled in the art in view of the teachings. set forth herein. It is therefore to be understood that all such variations, modifications and changes are believed to fall within the scope of the present invention as defined by the appended claims.

What is claimed is:

1. A thermal treatment system for thermally treating a sterile medium in a sterile surgery environment, said system comprising:
    a system housing including a top surface;
    a basin disposed on said top surface for containing said sterile medium;
    a thermal treatment unit to thermally treat said sterile medium disposed in said basin; and
    a controller selectively manipulable by a user to control system operation, wherein said controller is disposed on an external sidewall of said system housing and controls operation of said thermal treatment unit to thermally treat said sterile medium in accordance with said manipulation.

2. The system of claim 1, wherein said controller is selectively manipulable through a surgical drape that covers and substantially conforms to said basin and at least a portion of said external sidewall including said controller.

3. The system of claim 1, wherein said controller includes an input device to facilitate entry of a desired temperature into said controller to control thermal treatment of said sterile medium disposed within said basin to the desired temperature.

4. The system of claim 1, further comprising a temperature indicator disposed on said system housing to selectively indicate temperature information including at least one of a measured temperature and a desired temperature for said sterile medium disposed in said basin.

5. The system of claim 4, wherein said temperature indicator includes a digital display to display said temperature information.

6. The system of claim 5, wherein said digital display is disposed on said external sidewall of said system proximate said controller and displays temperature information in a manner sufficient to be perceived through a surgical drape that covers and substantially conforms to said basin and at least a portion of said external sidewall including said digital display.

7. A thermal treatment system for thermally treating a sterile medium in a sterile surgery environment, said system comprising:
    a system housing including a top surface;
    a basin disposed on said top surface for containing said sterile medium;
    a thermal treatment unit to thermally treat said sterile medium disposed in said basin;
    a controller disposed on said system housing and selectively manipulable by a user to control system operation, wherein said controller controls operation of said thermal treatment unit to thermally treat said sterile medium in accordance with said manipulation; and
    a temperature display disposed on said system housing to display temperature information including at least one of a measured temperature and a desired temperature for said sterile medium disposed in said basin.

8. The system of claim 7, wherein said temperature display digitally displays said temperature information.

9. The system of claim 7, wherein said temperature display is disposed on an external wall of said system housing and displays temperature information in a manner sufficient to be perceived through a surgical drape that covers and substantially conforms to said basin and at least a portion of said external wall including said temperature display.

10. The system of claim 7, wherein said controller includes an input device to facilitate entry of the desired temperature into said controller to control thermal treatment of said sterile medium disposed within said basin to the desired temperature.

11. In a thermal treatment system for thermally treating a sterile medium including a system housing including a top surface, a basin disposed on said top suffice to contain said sterile medium and a thermal treatment unit to thermally treat said sterile medium disposed in said basin, a method of controlling said system to thermally treat said sterile medium comprising the step of:
    (a) controlling said thermal treatment unit to thermally treat said sterile medium in accordance with user manipulation of a controller disposed on an external sidewall of said system housing.

12. The method of claim 11, wherein step (a) further includes:
    (a.1) controlling said thermal treatment unit to thermally treat said sterile medium in accordance with user manipulation of said controller through a surgical drape that covers and substantially conforms to said basin and at least a portion of said external sidewall including said controller.

13. The method of claim 11, wherein step (a) further includes:
    (a.1) controlling thermal treatment of said sterile medium disposed within said basin to a desired temperature in accordance with user entry of the desired temperature into said controller via an input device.

14. The method of claim 11, wherein said system further includes a temperature indicator disposed on said system housing, and the method further comprises:
    (b) selectively indicating temperature information via said temperature indicator, wherein said temperature information includes at least one of a measured temperature and a desired temperature for said sterile medium disposed in said basin.

15. The method of claim 14, wherein said temperature indicator includes a digital display, and step (b) further includes:
    (b.1) digitally displaying said temperature information via said digital display.

16. The method of claim 15, wherein said digital display is disposed on said external sidewall of said system housing proximate said controller and step (b.1) further includes:
    (b.1.1) displaying temperature information in a manner sufficient to be perceived through a surgical drape that covers and substantially conforms to said basin and at least a portion of said external sidewall including said digital display.

17. In a thermal treatment system for thermally treating a sterile medium including a system housing including a top surface, a basin disposed on said top surface to contain said sterile medium and a thermal treatment unit to thermally treat said sterile medium disposed in said basin, a method of controlling said system to thermally treat said sterile medium comprising the steps of:

(a) controlling said thermal treatment unit to thermally treat said sterile medium in accordance with user manipulation of a controller disposed on said system housing; and (b) displaying temperature information via a temperature display disposed on an external wall of said system housing, wherein said temperature information includes at least one of a measured temperature and a desired temperature for said sterile medium disposed in said basin.

18. The method of claim 17, wherein step (b) further includes:

(b.1) digitally displaying said temperature information via said temperature display.

19. The method of claim 17, wherein step (b) further includes:

(b.1) displaying temperature information in a manner sufficient to be perceived through a surgical drape that covers and substantially conforms to said basin and at least a portion of said external wall including said temperature display.

20. The method of claim 17, wherein step (a) further includes:

(a.1) controlling thermal treatment of said sterile medium disposed within said basin to a desired temperature in accordance with user entry of the desired temperature into said controller via an input device.

* * * * *